(12) United States Patent
Montes de Oca Balderas et al.

(10) Patent No.: US 9,662,817 B2
(45) Date of Patent: May 30, 2017

(54) METHOD AND APPARATUS FOR INJECTION MOULDING OF AN ELONGATED HOLLOW ARTICLE

(71) Applicant: Hollister Incorporated, Libertyville, IL (US)

(72) Inventors: Horacio Montes de Oca Balderas, Ballina (IE); Gottfried Steiner, Spielberg (AT); Herbert Eichler, Spielberg (AT)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 14/431,210

(22) PCT Filed: Sep. 27, 2013

(86) PCT No.: PCT/US2013/062205
§ 371 (c)(1),
(2) Date: Mar. 25, 2015

(87) PCT Pub. No.: WO2014/052770
PCT Pub. Date: Apr. 3, 2014

(65) Prior Publication Data
US 2015/0273747 A1 Oct. 1, 2015

(30) Foreign Application Priority Data

Sep. 28, 2012 (EP) ..................................... 12186505
May 3, 2013 (EP) ..................................... 13166389

(51) Int. Cl.
*B29C 45/17* (2006.01)
*B29C 45/26* (2006.01)
(Continued)

(52) U.S. Cl.
CPC ...... *B29C 45/1751* (2013.01); *B29C 45/1703* (2013.01); *B29C 45/1705* (2013.01);
(Continued)

(58) Field of Classification Search
CPC ..................... B29C 2045/5695; B29C 49/022
(Continued)

(56) References Cited

U.S. PATENT DOCUMENTS 2,443,053 A   6/1948  Parmelee
2,801,444 A * 8/1957  Lorenian ................. B29C 45/56
                                                    264/255

(Continued)

FOREIGN PATENT DOCUMENTS

DE      1111810    *  7/1961
DE    202008014672    2/2009
(Continued)

OTHER PUBLICATIONS

European Search Report and Opinion, counterpart EP Appl. No. 12186505, dated Feb. 28, 2013.
(Continued)

*Primary Examiner* — Jill Heitbrink
(74) *Attorney, Agent, or Firm* — Cook Alex Ltd.

(57) ABSTRACT

The present disclosure concerns an apparatus and a method for injection molding of an elongated hollow article, such as a urinary catheter, said apparatus comprising a heated central mold with an inlet opening for entering liquid molding compound into a substantially tubular cavity formed in said central mold; an elongated central mold core which is provided in the tubular cavity and extends beyond said tubular cavity and into a tip mold cavity of a tip mold part which is aligned with the tubular mold cavity in the longitudinal axis of the central mold core; wherein the tip mold
(Continued)

part is moveable in a linear movement in a direction along the longitudinal axis of the elongated central mold core.

17 Claims, 40 Drawing Sheets

(51) Int. Cl.
B29C 47/00 (2006.01)
B29C 49/02 (2006.01)
B29C 45/56 (2006.01)
B29L 31/00 (2006.01)
B29L 23/00 (2006.01)

(52) U.S. Cl.
CPC ........ *B29C 45/261* (2013.01); *B29C 47/0023* (2013.01); *B29C 45/56* (2013.01); *B29C 49/022* (2013.01); *B29C 2045/5695* (2013.01); *B29L 2023/00* (2013.01); *B29L 2031/7542* (2013.01)

(58) Field of Classification Search
USPC .................................................. 264/328.11
See application file for complete search history.

(56) References Cited

U.S. PATENT DOCUMENTS

| | | | |
|---|---|---|---|
| 2,969,563 A | 1/1961 | Hendry | |
| 3,296,345 A * | 1/1967 | Dietz | B29C 49/20 264/274 |
| 3,328,498 A * | 6/1967 | Cheney | B29C 47/20 264/152 |
| 3,329,996 A * | 7/1967 | Marcus | B29C 47/22 264/526 |
| 3,394,209 A * | 7/1968 | Cheney | B29C 47/20 264/527 |
| 3,466,701 A * | 9/1969 | Cheney | B29C 47/20 425/525 |
| 3,725,522 A | 4/1973 | Sheridan et al. | |
| 4,188,179 A * | 2/1980 | Linss | B29C 47/22 264/539 |
| 4,750,877 A | 6/1988 | McFarlane | |
| 4,806,093 A * | 2/1989 | Linss | B29C 49/022 215/370 |
| 5,316,706 A | 5/1994 | Muni et al. | |
| 5,358,580 A | 10/1994 | Miyamura et al. | |
| 5,409,644 A | 4/1995 | Martin et al. | |
| 5,547,364 A | 8/1996 | Wong et al. | |
| 5,558,737 A | 9/1996 | Brown et al. | |
| 5,614,136 A | 3/1997 | Pepin et al. | |
| 5,762,631 A | 6/1998 | Klein | |
| 5,780,073 A | 7/1998 | Chen et al. | |
| 5,851,464 A | 12/1998 | Davila et al. | |
| 5,853,518 A | 12/1998 | Utas | |
| 6,086,970 A | 7/2000 | Ren | |
| 6,280,788 B1 | 8/2001 | Rakhorst et al. | |
| 7,399,444 B2 | 7/2008 | Skinner et al. | |
| 7,431,876 B2 | 10/2008 | Mejlhede et al. | |
| 7,871,261 B2 | 1/2011 | Steiner et al. | |
| 7,910,044 B2 | 3/2011 | Steiner et al. | |
| 8,048,058 B2 | 11/2011 | Fulford | |
| 8,123,892 B2 | 2/2012 | Morris et al. | |
| 2002/0084551 A1 | 7/2002 | Lee | |
| 2003/0044484 A1 | 3/2003 | Goral et al. | |
| 2004/0159966 A1 | 8/2004 | Yamaguchi | |
| 2004/0241364 A1 | 12/2004 | Zihlmann | |
| 2005/0104255 A1 | 5/2005 | Mejlhede et al. | |
| 2008/0027414 A1 | 1/2008 | Tanghoj et al. | |
| 2010/0221500 A1 | 9/2010 | Steiner et al. | |
| 2011/0180969 A1 | 7/2011 | Sansoucy | |
| 2012/0150130 A1 | 6/2012 | Triel et al. | |

FOREIGN PATENT DOCUMENTS

| | | |
|---|---|---|
| DE | 102008052950 | 4/2009 |
| DE | 102008052951 | 4/2009 |
| EP | 0371497 | 6/1990 |
| EP | 0465660 | 1/1992 |
| EP | 0489335 | 6/1992 |
| EP | 618059 | 10/1994 |
| EP | 662385 | 7/1995 |
| EP | 0824930 | 2/1998 |
| EP | 0850655 | 7/1998 |
| EP | 1034811 | 9/2000 |
| EP | 1110711 | 6/2001 |
| EP | 1208955 | 5/2002 |
| EP | 1935614 | 6/2008 |
| EP | 2335767 | 6/2011 |
| EP | 2445565 | 5/2012 |
| EP | 2712721 | 4/2014 |
| GB | 2230702 | 10/1990 |
| WO | WO 91/14473 | 10/1991 |
| WO | WO 97/10940 | 3/1997 |
| WO | WO2004/067076 | 8/2004 |
| WO | WO 2009/048423 | 4/2009 |
| WO | WO2009/117270 | 9/2009 |
| WO | WO2010/149175 | 12/2010 |
| WO | WO 2013/127718 | 9/2013 |
| WO | WO 2013/127725 | 9/2013 |

OTHER PUBLICATIONS

International Search Report and Written Opinion, counterpart PCT Appl. No. PCT/US2013/062205, dated Nov. 4, 2013.
Brown, S. et al., Extrusion of Precision Small-Diameter Plastic Tubing for Medical Applications, *Medical Device Technology*, 3 (7), pp. 34-40 (1992).
Callari, J., Dies Easy to Adjust, *Plastics World*, 53 (2), p. 14 (1995).
Colbert, J., Concepts of Precision Tube Extrusion for Medical and Healthcare Applications, *Antec 95*, vol. III, pp. 3375-3382 (1995).
Dowler, B. et al., How Low Can You Go? Optimising Cooling of Small Injection Moulded Parts, *Antec 97*, vol. 1, pp. 946-953 (1997).
Ferrandino, M., Tubing Extrusion Made Easier, Part 1, *Medical Device Technology*, 15 (8), pp. 12-15 (2004).
Gupta, A. et al., Influence of a Rotating Tip on the Properties of Tubing Made Using a Crosshead Tubing Die, *International Polymer Processing*, 14 (1), pp. 51-56 (1999).
Kirkland, C., Nanomoulding Meets the Medical Catheter Tip, *Injection Molding*, 9 (10), pp. 79-80 (Oct. 2001).
Machado, A., Multi Lumen Die Design and Techniques, *Conference Medical Manufacturing*, Paper 2.2.3 (1990).
Martini, L. G. et al., Manufacturing High Quality Urinary Catheters, *Medical Device Technology*, 20 (1), pp. 18-19 (2009).
Mori, K. et al., Development of Polymer-Molding-Releasing Metal Mold Surfaces with Perfluorinated-Group-Containing Polymer Plating, *Journal of Applied Polymer Science*, 90 (9), pp. 2549-2556 (2003).
O'Neil, C., Selecting Materials for Mission-Critical Catheters, *European Medical Device Technology*, 1 (9), pp. 48-55 (2010).
Person, T. J. et al., The Effect of Die Materials and Pressure-Dependent Slip on the Extrusion of Linear Low-Density Polyethylene, *Journal of Rheology*, 41 (2), pp. 249-265 (1997).
Schut, J. H., Moving Die Parts Change Profile Shapes "On The Fly", *Plastics Technology*, 52 (4), pp. 45, 47 (2006).
Schut, J. H., Medical Tubing: Tinier Than Ever and Much More Complex, *Plastics Technology*, 53 (4), pp. 70-73 (2007).
Stein, O., Extrusion of Medical Tubing, *Plastics in Medical Technique*, pp. 179-191 (2002).
No Author, Cool Small Mold Cores Faster with New Water Transfer System, *Plastics Technology*, 24 (8), pp. 48-49 (1978).
No Author, One-Piece Catheter, *Plastics and Rubber Weekly*, 1264, p. 8 (1988).
No Author, One-Piece Catheter Cuts Manufacturing Costs, *Biomedical Materials*, pp. 4-5 (1990).

(56) References Cited

OTHER PUBLICATIONS

No Author, New Dies Fine-Tune Tiniest Medical Tubes, *Plastics Technology*, 48 (9), p. 17 (2002).
No Author, Medical Tubing Can Be Configured on the Fly, *British Plastics and Rubber*, p. 10 (2006).
Colbert, J., High Quality Tube Extrusion for the Medical Device Industry, *Polymers for the Medical Industry*, paper 4 (1999).
Comim, L. M. et al., Effect of the Extrusion Process on the Bactericidal Performance of Biocidal Polypropylene Catheters, *Polymer-Plastics Technology and Engineering*, 51(3), pp. 289-295 (2012).
Kazmierska, K. et al., Determination of Urethral Catheter Surface Lubricity, Journal of Materials Science, Materials in Medicine, 19(6), pp. 2301-2306 (2008).
Zhao, Danyang et al., Numerical Simulation and Experimental Study of Polymer Micro Extrusion Flow, *IEEE International Conference on Mechatronics and Automation*, pp. 3155-3160 ( 2009).
Ahmed, N. et al., A Hydrophilic Technology for Intermittent Urinary Catheters, Medical Device Technology, 19 (1), pp. 17-19 (2008).
Bales, S. J., Know Your Mold Coatings, Plastics Technology, 50 (12), pp. 52-57 (2004).
Baumeister, C., et al., Excellent Catheter Coupling. Raumedic Develops and Produces a Component of 2K Injection Moldings for Medicinal Applications, Kunststoffberater, 50 (5), pp. 38-40 (2005).
Beddus, D., Extruder Theory and Die Design for Medical Tubing, Conference Medical Manufacturing, Paper 2.2.1 (1990).
Berg, G. et al., Chrome Nitride Coatings for Applications in Plastics Processing, International Polymer Processing, 14 (2), pp. 122-127 (1999).
Callari, J. J., Precision Processing: It's All in the Details, Plastics World, 53 (2), pp. 35-38 (1995).
Chen, S. C. et al., Efficiencies of Various Mold Surface Temperature Controls and Their Effects on the Qualities of Injection Molded Parts, ANTEC 2006, 64th SPE Annual Conference, pp. 1280-1284 (2006).
Daniels, U. et al., How Injection Moulding Tool Coating Affects the Demoulding Force, Kunststoffe/German Plastics, 79 (1), pp. 42-44 (1989).

Fallon, M., Resins Flow Better in TiN-Coated Molds, Plastics Technology, 36 (6), pp. 41-43 (1990).
Farzaneh, S. et al., Critical Factors in Extruding Catheter Tubing From Polyamide, Medical Device & Diagnostic Industry, 24 (11), pp. 54-60 (2002).
Kaiser, W. et al., Injection Moulds. Titanium Nitride Coating Improves Injection Moulding of Thermoplastics, Plastverarbeiter, 40 (10), pp. 81-91 (1989).
Navabpour, P. et al., Evaluation of Non-Stick Properties of Magnetron-Sputtered Coatings for Moulds Used for the Processing of Polymers, Surface & Coatings Technology, 201 (6), pp. 3802-3809 (2006).
Reilly, J. F., Fast Fourier Transform Analysis of Melt Fractured Extrudate, Conference Polymer Rheology 99, paper 6 (1999).
Shearer, G., et al., Extrusion of LLDPE Through Polypropylene Coated Dies, Annual Technical Conference, vol. I, pp. 73-77 (1999).
No Author, BM Equips Catheter Facility, Plastics and Rubber Weekly, 1817, p. 9 (1999).
No Author, Enhancing the Economic Efficiency in the Production of Catheter Hoses, Kunststoffe-Synthetics, 50 (1), pp. 14-15 (2003).
No Author, Extrusion Plants for Continuous Hollow Profile Manufacture, Plastverarbeiter, 49 (10), p. 152 (1998).
No Author, High-Tech Plant for High Precision Flexible Tube Extrusion for Cardiac Catheters Application, Plastverarbeiter, 49 (7), pp. 26-27 (1998).
No Author, Manufacturing Medical Catheter Tubes, Extrusion, 10 (5), pp. 18-19 (2004).
No Author, Surface Treatments Extend Tool Life, Plastics Technology, 43 (3), p. 29 (1997).
International Preliminary Report on Patentability, counterpart PCT Appl. No. PCT/US2013/062205, dated Mar. 31, 2015.
Examination Report, counterpart Australian Appl. No. 2013323339, dated Nov. 26, 2015.
Office Action, counterpart Canadian Appl. No. 2,889,820, dated Mar. 10, 2016.
Office Action, counterpart Canadian Appl. No. 2,889,820, dated Sep. 29, 2016.

* cited by examiner

METHOD AND APPARATUS FOR INJECTION MOULDING OF AN ELONGATED HOLLOW ARTICLE

The present application is a U.S. National Stage of PCT International Patent Application No. PCT/US13/62205, filed Sep. 27, 2013, which claims priority to EP Application No. 12186505.9, filed Sep. 28, 2012, and Ser. No. 13/166,389.0, filed May 3, 2013, all of which are hereby incorporated herein by reference.

The present disclosure relates to a method and apparatus for injection moulding of an elongated hollow article, such as a urinary catheter.

BACKGROUND ART

As explained in U.S. Pat. No. 4,750,877 there is a need in the art of moulding plastic products to be able to mould a plastic part having a relatively small diameter hole extending therethrough.

Especially in the field of medical products, such as catheters, it is important to exert great care in maintaining the constant diameters of both the outer surface and the central hole extending through a catheter product since this has the effect of maintaining a substantially straight shank in the finished tubular product. Also, the product must be constructed to have a consistent flex pattern and avoid "kinking" when bent or flexed. Often, such moulded plastic parts are required to have a thin wall of necessarily constant thickness with a longitudinally extending channel extending therethrough.

Previously, especially in the art of injection moulding, when plastic is melted, and forced to flow into a cavity about a fine, small diameter core, the pressure of injection forcing the melt into the mould cavity if not adequately balanced during the moulding operation tends to cause the thin diameter core to be displaced from its substantially centred, straight line configuration relative to the central axis of the mould cavity. This displacement is of course undesirable since a straight line configuration of the central hole as well as the shank portion of the product is required. Such displacement of the core pin relative to the interior surface of the mould cavity is also frequently caused by what may be considered an imbalance in the flow characteristics of the hot melt as it enters the mould cavity and passes along the length thereof in substantially surrounding relation to the core pin. Such imbalance may be caused by a number of factors but also has the tendency to cause uneven forces to be exerted on the core pin tending to cause its displacement from the aforementioned and preferred straight line configuration. For these reasons, the prior art has generally been limited to relatively short tubular lengths in relation to the diameter of the hole through it. If, for example, the tubular product is to be relatively long, which is quite common in the medical industry, a small hole, especially a hole in a thin walled tube is extremely difficult to make with any great degree of accuracy. In addition, different materials provide different problems.

Another problem generally associated with the injection moulding technique of products of the type referred to above is the breakdown in the intensity of the plastic material utilized to form the tubular product when the material is forced to travel along what may be referred to as a circuitous path from the point of leaving the injection nozzle to the point of entering and passing along the length of the mould cavity. This is particularly true when the plastic material, after being melted, is forced to flow along a circuitous path or a path including one or more right angles at a relatively high speed. Attempts to slow the speed of injection of the inflowing melt however have met with little success especially in the formation of thin walled tubular products. This is primarily due to the fact that the melt rapidly cools and therefore solidifies as it flows along the length of the mould cavity especially at slow speeds. Accordingly, when using injection moulding techniques at such slow speeds, attempts have been made to raise the temperature of the plastic material to a somewhat higher than normal temperature, prior to injection to overcome the problems of the prior art. This higher temperature results in a degradation of many plastic materials which has obvious disadvantages in the making of thin walled tubular products.

U.S. Pat. No. 2,443,053 discloses a method and an apparatus for manufacturing hollow cylindrical plastic articles with a moving core, which is moved during the injection of moulding material through an annular inlet in the stationary outer moulding member. However, according to the moulding technique disclosed herein, the first end section of the article is formed whereafter a tubular section of the article is formed. However, there are limitations to which designs the article can have when moulded according to this method as only the front end of the article can be provided with a special design as the rest of the article must have a cylindrical shape.

From U.S. Pat. No. 7,871,261 and U.S. Pat. No. 7,910,044 a method and an injection moulding apparatus for producing profiled elongated articles are disclosed where a moving inlet is provided for a moving moulding core.

From EP 1 116 567 there is known a gas assisted injection moulding technique. However, this technique only allows making short catheters.

SUMMARY

As explained above, one of the technical factors limiting the use of conventional injection moulding for catheter manufacture is the high injection pressures required to fill the cavity and the difficulty of producing long tubular parts, e.g. up to and in excess of 40 cm, with adequate internal and outer diameter tolerances and good reproducibility. Therefore, it is an object of the disclosure to provide an improved method and apparatus for injection moulding of elongated hollow articles, in particular for the manufacture of urinary catheters.

The disclosure comprises a method and an apparatus for injection moulding of an elongated hollow article, such as a urinary catheter, said apparatus comprising a heated central mould with an inlet opening for entering liquid moulding compound into a substantially tubular cavity formed in said central mould; an elongated central mould core which is provided in the tubular cavity and extends beyond said tubular cavity and into a tip mould cavity of a tip mould part which is aligned with the tubular mould cavity in the longitudinal axis of the central mould core; wherein the tip mould part is moveable in a linear movement in a direction along the longitudinal axis of the elongated central mould core.

Hereby an injection moulding technique with a moving mould is provided. The moving mould provides a drag force to transport a viscous melt of moulding material to fill the elongated cavity and minimizing the injection pressure required to make an article with a predetermined tip design at one end and a predetermined shape at the other end, in particular a tipped urinary catheter, including a funnel connector portion of the opposite end, produced in a single polymer processing operation.

It is preferred that the movable tip mould is movable in a linear direction from a first position where the tip mould is abutting the outer mould with the tip mould cavity aligned with the mould cavity to a second position at a predetermined distance from said first position via a sledge.

In a preferred embodiment, the elongated central mould core is moveable and adapted to be moved in the same direction and together with the tip mould part. In addition, it may be advantageous that the elongated central mould core is moved by being pushed by a second elongated central mould core which will eventually provide the elongated mould core for the subsequent moulding cycle. Accordingly, the elongated mould core is ejected together with the moulded article by the insertion and positioning of the second elongated central mould core. This is advantageous since the elongated mould core acts as a mandrel for the moulded product which facilitates the handling of the product during the subsequent processing steps, such as surface coating, etc.

In an embodiment of the disclosure, the tubular cavity is cylindrical with a circular cross-section. However, it is realised that other cross-sectional shapes may be provided.

Advantageously, the disclosure provides the option of providing at least a section of the inner surface of the outer mould with a predetermined patterning for moulding such patterning on the surface of the article.

In order to assist in ensuring a predetermined inner surface of the article, it is found advantageous in an embodiment that the elongated mould core is provided with a fluid channel, which is in flow connection with a fluid source, such as a pressurised air source providing air through the fluid channel. The fluid channel is in flow communication with the first end of the mould cavity at the distal end mould core, and in connection with the fluid source, such as the pressurised air source and at the second end of the fluid channel.

Using the method and apparatus according to the present disclosure is found particularly advantageous that the elongated hollow article is a catheter with the first end geometry being the proximal tip end of the catheter and the second end being the funnel-shaped connector end of the catheter.

According to a further aspect, there is provided an apparatus and a method for injection moulding of an elongated hollow article, such as a urinary catheter, where said apparatus comprises a heated central mould with an inlet opening for entering liquid moulding compound into a substantially tubular cavity formed in said central mould;

an elongated central mould core which is provided in the tubular cavity and extends beyond said tubular cavity; and a movable tip mould part, which is provided with a tip mould cavity and which is arranged for linear movement in a direction substantially similar to the orientation of the elongated central mould core, and wherein said elongated central mould core is stationary and provided with a fluid channel which is in flow communication with the tip mould cavity at the distal end elongated central mould core, and in connection with a fluid source and at the second end of the fluid channel.

The method of injection moulding of an elongated hollow article, such as a urinary catheter, according to this third aspect comprises the steps of:

injecting a liquidised moulding compound into a mould comprising a heated central mould with an inlet opening for entering the liquidised moulding compound into a substantially tubular cavity formed in said central mould, said mould further comprising an elongated central mould core which is provided in the tubular cavity and extending beyond said tubular cavity; and moving a tip mould part provided with a tip mould cavity which is aligned with the mould cavity in a linear direction from a first position where the tip mould is abutting the mould to a second position at a predetermined distance from said first position via a sledge; whereby said elongated central mould core is stationary and provided with a fluid channel which is in flow communication with the tip mould cavity at the distal end elongated central mould core, and in connection with a fluid source and at the second end of the fluid channel.

This embodiment may be advantageous since the moulding apparatus according to this process can be adopted for producing elongated articles, such as urinary catheters, of a variety of lengths, in principle any lengths. This method and apparatus is found particular advantageous that the elongated hollow article is a catheter with the first end geometry being the proximal tip end of the catheter and the second end being the funnel-shaped connector end of the catheter. Hereby, the costs of manufacturing such articles can be reduced since the articles can be produced in a reduced amount of moulding processes, preferably a single moulding process.

The elongated central mould core is preferably temperature controlled for maintaining an elevated temperature, such as a temperature similar to that of the heated central mould. More particularly, the elevated temperature is above the melting temperature of the liquid mould compound, such as between +130° C. and +350° C. depending on the polymer material used for the moulding process.

Similarly, the movable tip mould part is preferably temperature controlled for maintaining a temperature lower than of that the heated central mould. In particular, the temperature of the movable tip mould part is kept below the melting temperature for the mould compound material, such as between +20° C. and +130° C., which is also well below the glass temperature of the polymer materials used for moulding the article.

According to an embodiment, the fluid channel is in controlled flow connection with a pressurised air source providing pressurised air through the fluid channel into the inner volume of the moulded article during the moulding process. This air pressure inside the inner volume of the article stabilises the material of the moulded portion of the article during the moulding process as this portion leaves the inner support of the elongated mould core. This pressurised air helps solidifying the material and ensures the shape of the article even though the material may not yet be solidified immediately after leaving the heated elongated mould core.

According to the moulding in this embodiment, the movable tip mould is movable in a linear direction from a first position where the tip mould is abutting the outer mould with the tip mould cavity aligned with the mould cavity to a second position at a predetermined distance from said first position via a sledge. This ensures the formation of the tubular portion of the article in an extrusion moulding sub-process.

In a preferred embodiment, a set of cooling mould blocks is provided for radially inwardly encompassing and preferably also clamping the moulded portion of the article when the tip mould is approaching said second position. Furthermore, the cooling mould blocks are preferably provided with inner contacting surfaces resembling the shape of the tubular mould cavity. Hereby a rapid cooling of the article as well as the surface outer shape of the article is ensured.

In a further embodiment, the cooling mould blocks are formed with end contacting surfaces having an end section geometry. Particularly, the cooling mould blocks is provided with inner contacting surfaces resembling the shape of the tubular mould cavity and wherein the cooling moulding blocks are formed with end contacting surfaces having an end section geometry and pressurised air is supplied to form said end section geometry. Hereby, a sub-process of blow-moulding the second end shape of the elongated hollow article. This is particularly advantageous when producing a catheter with the first end geometry being the proximal tip end of the catheter and the second end geometry being the funnel-shaped connector end of the catheter.

According to a further embodiment, a gap between the cooling blocks and the outer mould is provided at the second position in which cutting means are provided for cutting the moulded article away from the mould. Hereby the moulded article is easily freed from the mould to complete the moulding cycle.

According to an aspect of the disclosure, the inlet member is preferably moving in the track of the outer mould, preferably in the upper half part, from a first position near the first end section of the cavity to a second position near the second end section of the cavity. Preferably, the movable inlet member is provided with an annular cooling section downstream the inlet opening and a heated section upstream the inlet opening. This is advantageous as it is hereby ensured that as the mould moves the injected polymer material solidifies, helping to support the mould core and hindering its deflection from the long axis of the article due to the injection pressure whereby a good control of the inner and outer diameter of the article during the moulding process is ensured.

Preferably, the limiter insert piston is moved together with the inlet member and the mould core until reaching its second end moulding position at the second end. Hereby the continuous moving injection mould can be finalised with a complex geometry at the second end.

According to an embodiment, the inlet member is moving together with (i.e. stationary relative to) the mould core. Moreover, the outer mould is preferably adapted to be moving during the injection moulding and the central mould core is stationary until the moulding process is finished whereafter the mould core is retracted for ejection of the moulded component.

It may be advantageous that the cavity of the second end is provided with an outer peripheral surface defining an end geometry larger than the outer diameter of the cavity of the cylindrical section of said cavity. This allows for the manufacture of more complex geometry at both ends of the elongated article.

DETAILED DESCRIPTION OF THE DRAWINGS

In the following the disclosure is described in more detail with reference to the drawings, in which.

Figure 1:
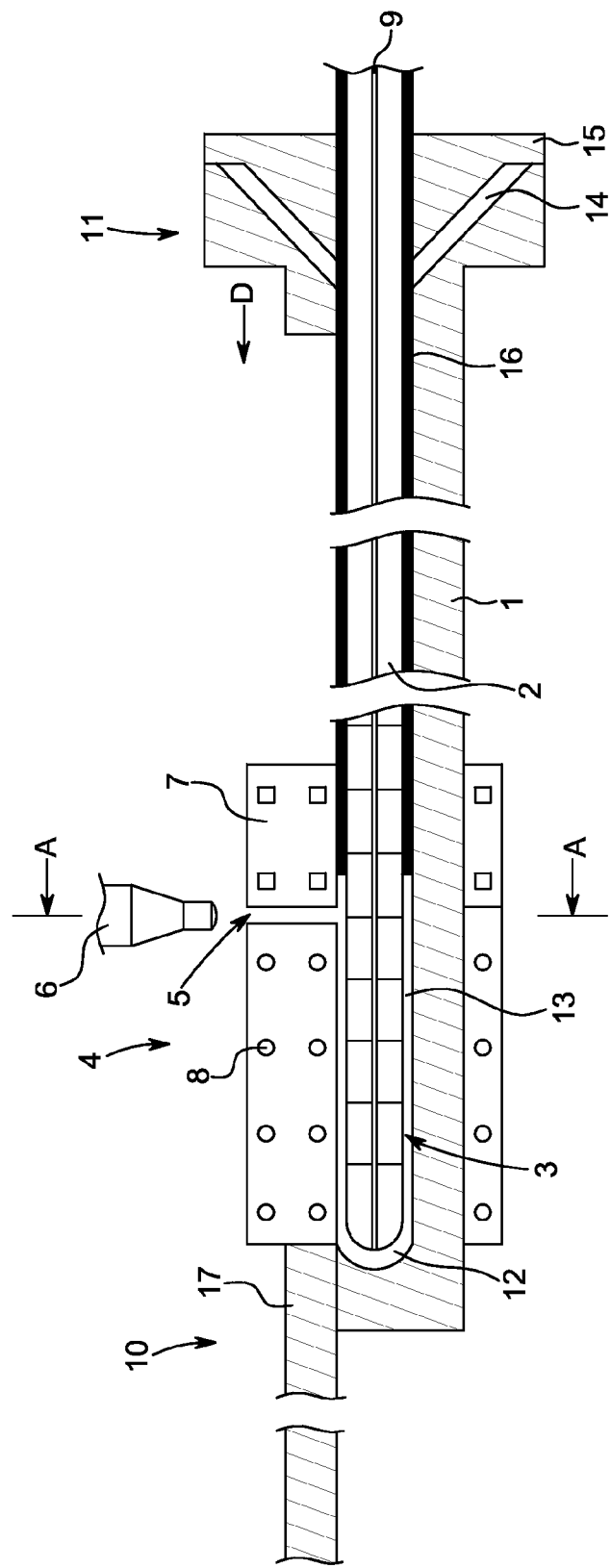
FIG. 1 is a schematic cross-sectional view of the initial position of the moulding apparatus according to a first embodiment of the disclosure.

With reference to FIG. 1, the moulding apparatus according to a first embodiment of the disclosure is shown. The apparatus comprises an elongated outer mould 1 and an elongated mould core 2 and a mould cavity 3 defined therebetween. The moulding apparatus has a first end 10 and a second end 11. At the first end mould cavity 12 is provided between the first end section of the outer mould 1 and the tip of the mould core 2. The mould cavity 3 extends from the first end section cavity 12 through a cylindrical mould cavity 13 to a second end mould cavity 14. At the second end 11 the outer mould 1 is provided with an end mould member 15 defining the second end geometry of the article as the end mould member 15 defines the end of the second end cavity 14. Surrounding the mould core 2 a cylindrical movable cavity limiting piston 16 is provided to define the end of the mould cavity 3 as the moulding process starts and until the final stage of the moulding process sets in (as explained below with reference to the further figures) where the moveable piston 16 is retracted to a position where flow communication to the second end cavity 14 is established (see FIGS. 5 and 6).

Figure 2:
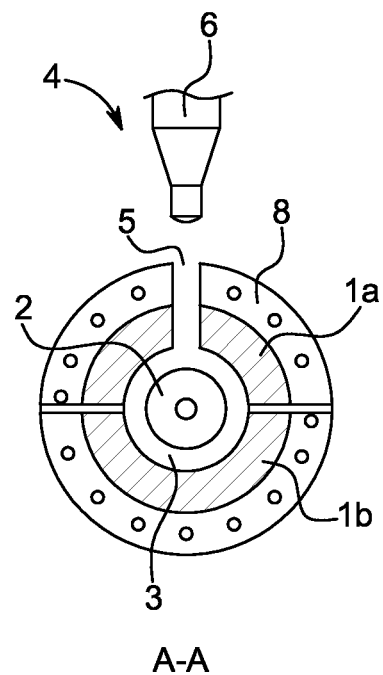
FIG. 2 is a cross-section along the section A-A of FIG. 1.
Figure 3:
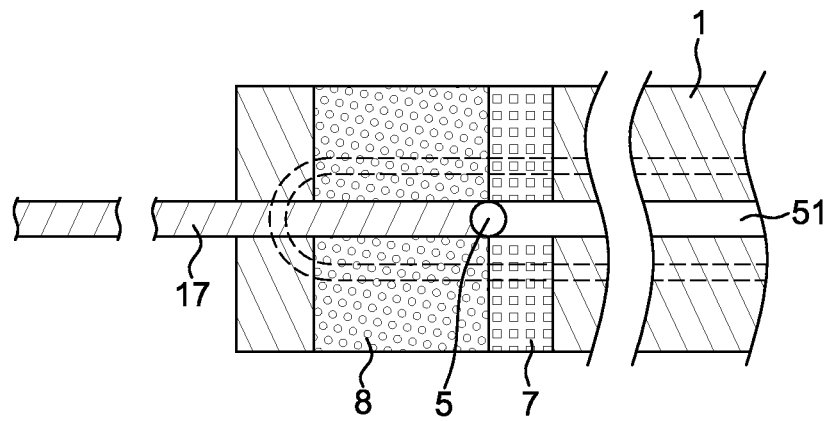
FIG. 3 is a top view of the moulding material inlet region of the apparatus of FIG. 1.

A moveable inlet member 4 is provided axially sliding along a track 51 of the outer mould member 1. This movable inlet member 4 is provided with an inlet opening 5 which is in flow communication with a liquid moulding material source 6. The inlet member 4 is adapted to move relative to the outer mould 1 from the start position at the first end 10 (see FIG. 1) to the finishing moulding process position at the second end (see FIG. 6). The inlet member 4 is provided with a cooling section 8 downstream the inlet opening 5 and a heating section 7 upstream the inlet opening 5. As shown in FIGS. 2 and 3, the outer mould is divided into an upper part 1a and a lower part 1b. In the upper part 1a a longitudinal track 51 is provided extending from the inlet opening 5 to the second end 11 of the mould 1. The inlet member 4 is provided on the outer side of the upper mould part 1a and the inlet opening 5 is positioned in the track 51.

In the first embodiment, the inlet member 4 is held stationary by a guide rail 17, which will close the mould downstream, having the shape of the track 51. The outer mould 1 is adapted to move relative to the inlet member 4 as well as the mould core 2 and the piston 16 which are also kept stationary during the moulding process.

Figure 4:
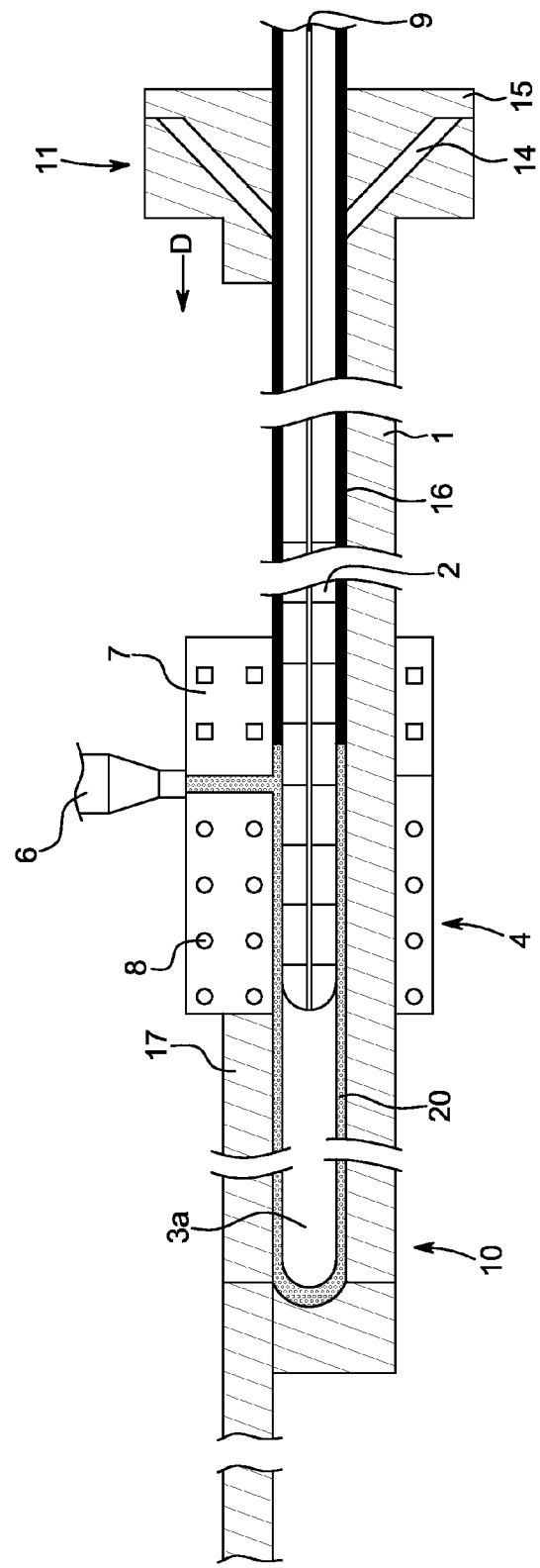
FIG. 4 is a schematic cross-sectional view of the moulding apparatus of FIG. 1 during the moulding process.

The mould core 2 is provided with a fluid channel 9 which has an opening to the mould cavity 3 at the distal first end 10 of the mould core 2. At the other end of the fluid channel 9 a pressurised air source (not shown) is provided. As the moulding process gets underway pressurised air is provided through the fluid channel 9 into the cavity 3 and into the hollow portion 3a of the article during the moulding (see FIG. 4). The pressurised air is provided inside the article during the moulding to assist to controlling the inner surface of the article as the mould core during the moulding process leaves the inner surface of the article exposed (see FIGS. 4 to 7). The fluid channel can also be used for any other fluid than air, such as a gas composition, a liquid mixture, a reactive liquid mixture, etc.

In an alternative to the shown embodiment, it is realised that the disclosure may also be used for the formation of profiles, such as tubes with multiple layers, for example a bi-layer, tri-layer tubes, etc. This may be achieved by providing more than one inlet member. Yet another embodiment allows making catheters with variable stiffness along the catheter length. Variable stiffness catheters facilitate catheter insertion and handling to the user. This embodiment requires injecting more than one polymer material.

The moulding process according to the first embodiment of the disclosure is illustrated in the FIGS. 1 and 4 to 9. In FIG. 1 the moulding apparatus is in its initial position where the outer mould 1 is positioned in a first position over the mould core 2 so that the first end cavity 12 forms the tip of the article to be produced in the moulding apparatus. The moulding process starts in this position (FIG. 1) as liquidised moulding material is injected through the inlet opening 5 and into the first end cavity 12 and fills the cavity to form the tip portion of the article. As the moulding material enters the cavity 13, it solidifies due to the cooling section 8 of the inlet member. When the first end cavity 12 is almost filled, the outer mould 1 begins to move in the direction D (see arrow D in FIGS. 1, 4 and 5) and the injected material 20 continues to flow and thereby form the cylindrical section 13 of the cavity 3 (see FIG. 4). Simultaneously, pressurised air is supplied through the fluid channel 9 in the mould core 2 in order to assist in forming the inner surface of the hollow article and avoid the formation of a vacuum inside the hollow portion 3a of the article which is now moulded and sits in the form as the mould core 2 is retracted from the inside of the article—or rather as the article is moved together with outer mould 1 relative to the stationary mould core 2. In order to facilitate the injection of liquid material into the cavity, the heating element 7 heats up the mould upstream the inlet opening 5 so that the material 20 is kept liquidised in the part of the cavity underneath the inlet 5 and is then cooled as the material 20 fills the mould cavity 3 downstream the inlet opening 5 so that the material solidifies.

Figure 5:
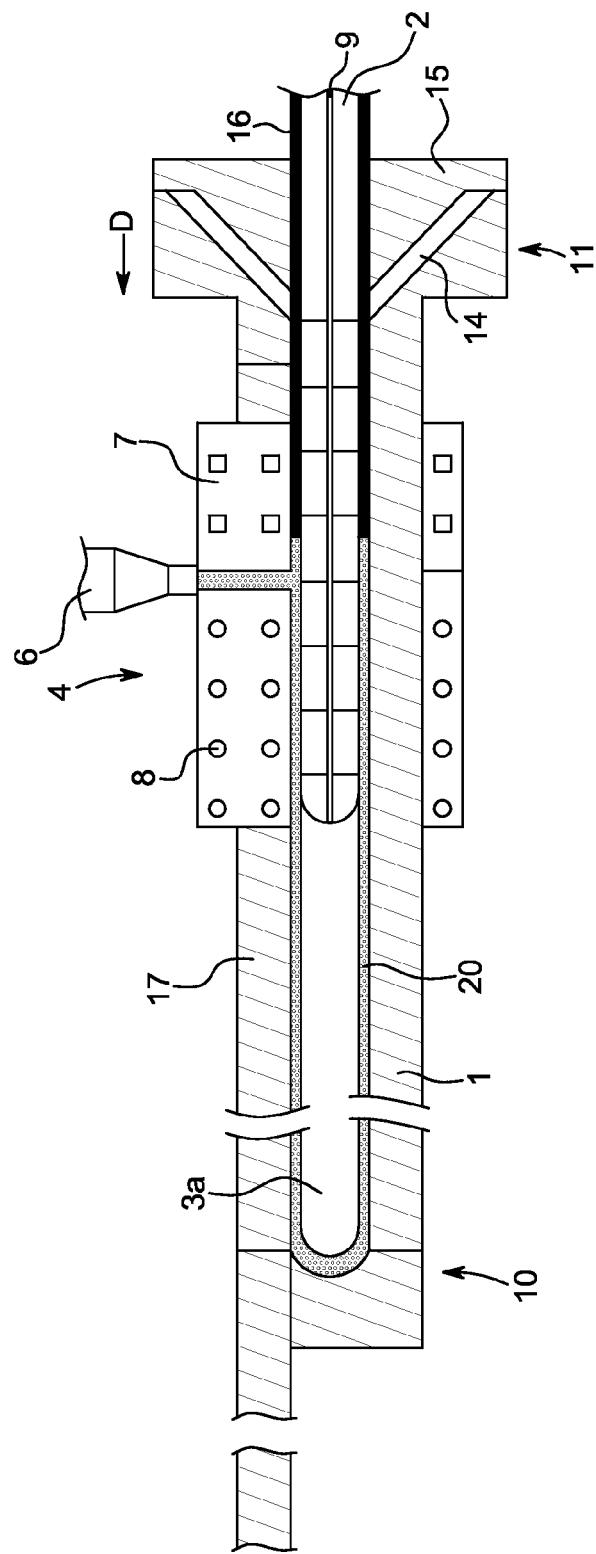
FIG. 5 is the same as the moulding process is nearing its completion.
Figure 6:
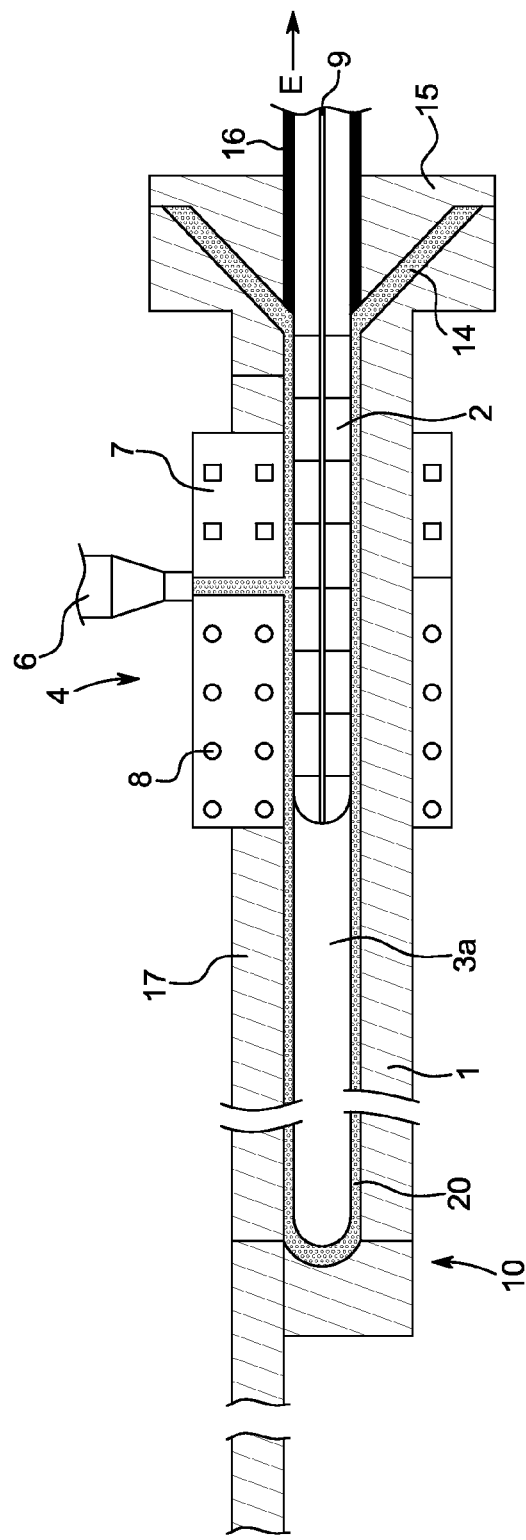
FIG. 6 is the moulding apparatus showing the moulding of the second end of the article.

The outer mould is moved until its final position which is shown in FIG. 5. When this position is reached, the outer mould 1 becomes stationary relative to the inlet member 4 and the mould core 2, but the movable limiter piston 16 will now be retracted as shown in FIG. 6 thereby establishing liquid flow communication with the second end cavity section 14 so that the second end portion of the article is moulded as the liquid moulding material 20 flows into this cavity section 14.

Figure 7:
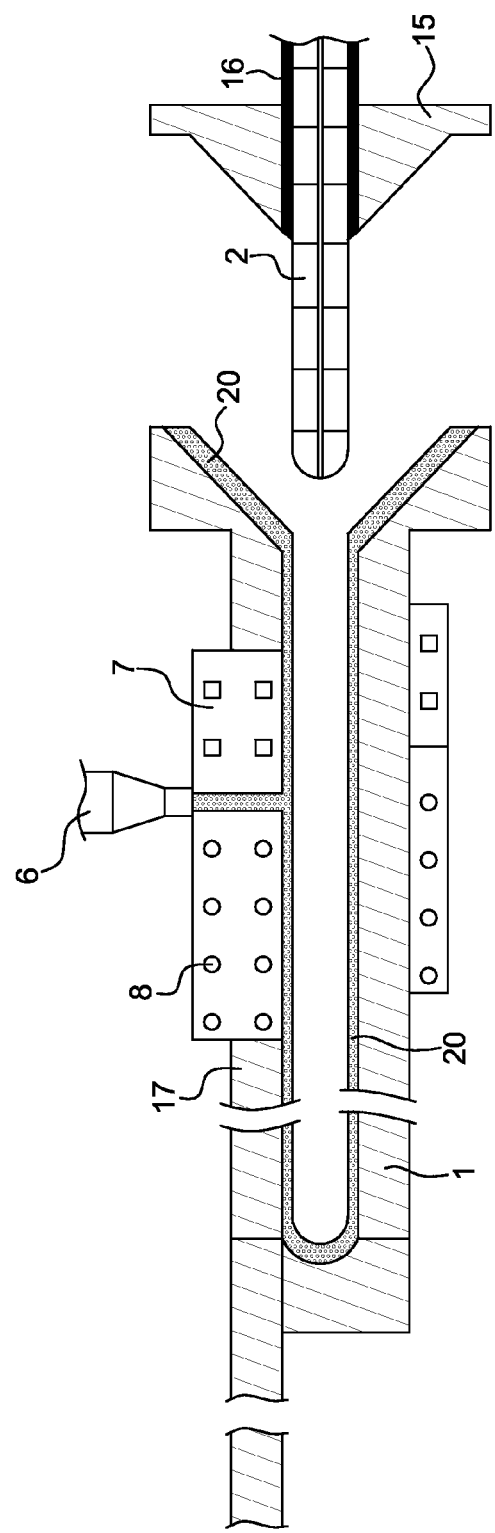
FIGS. 7 to 9 show the steps of ejecting the moulded article.
Figure 8:
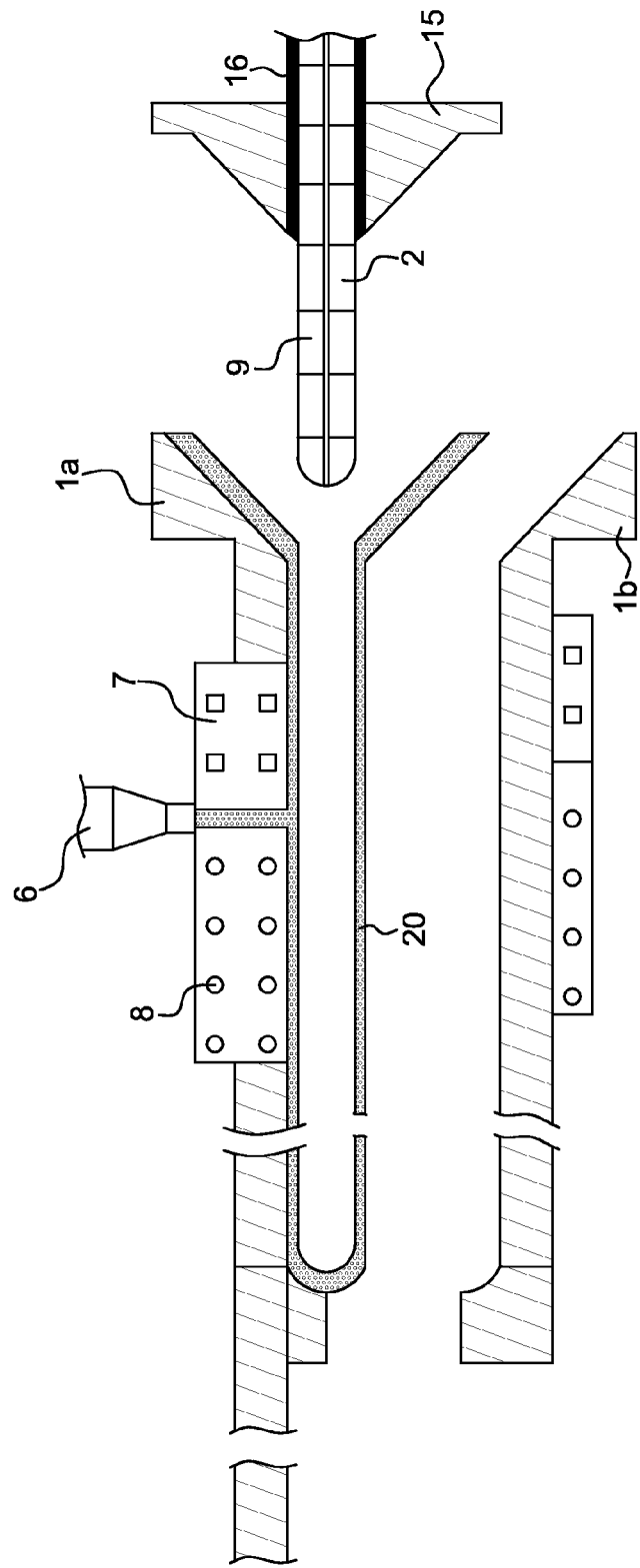
Figure 9:
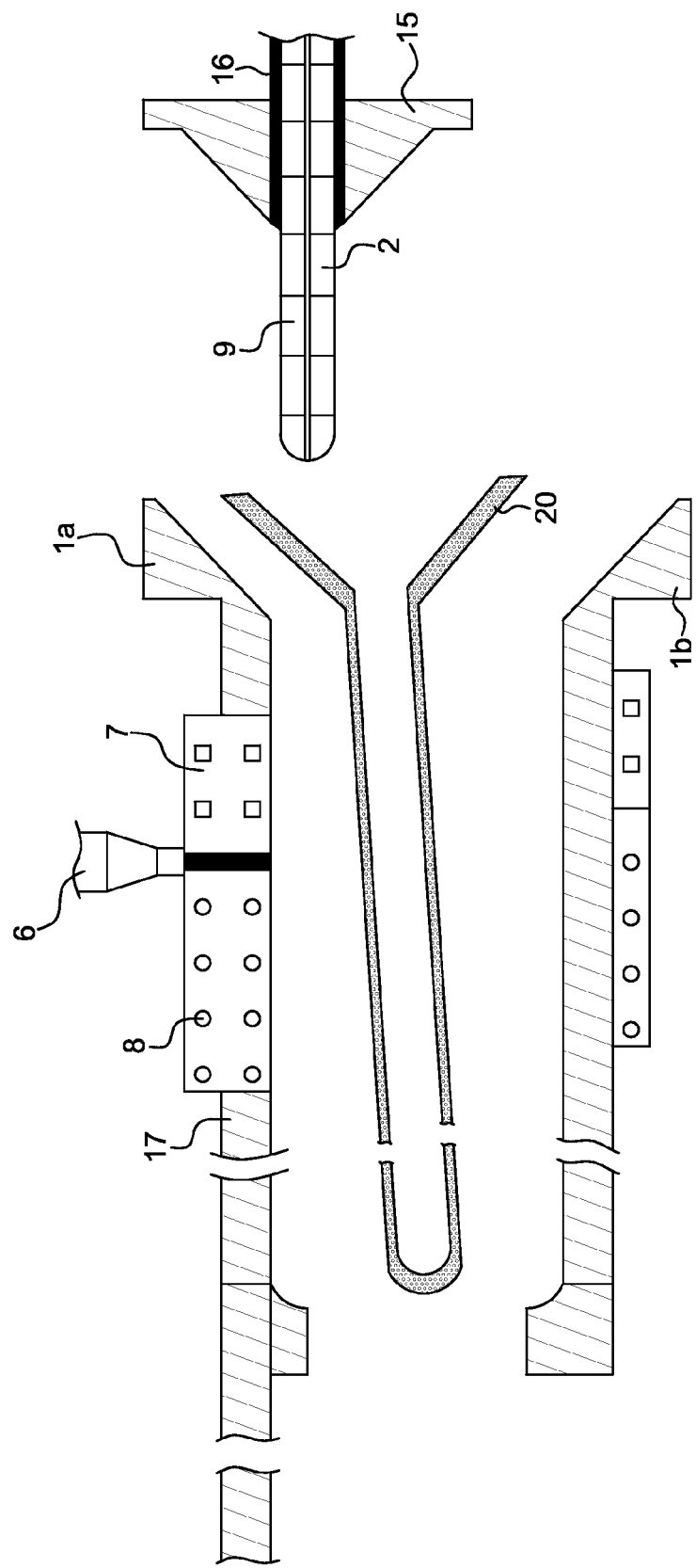

After the second end of the article 20 is moulded, the article 20 is ejected from the mould as shown in FIGS. 7 to 9. The mould core 2, the limiter piston 16 and the end mould member 15 are retracted so that these apparatus components are clear of the article (see FIG. 7) and then the outer mould 1 is disassembled (see FIG. 8) and the article 20 is expelled from the mould (see FIG. 9).

It is realised by the disclosure that the method and apparatus allows for adding a predetermined pattern on the catheter surface. For example the inner surface of the outer mould 1 (FIG. 1) can be machined or fabricated in such a way that it is possible to add a pattern so that when the molten polymer is moulded the catheter surface acquires this pattern. This pattern on the surface can facilitate application of wetting agents and coating layers that are typically used to improve lubricity of catheters and facilitate insertion into the human body With reference to FIGS. 10-20 a second embodiment of the disclosure is shown where the outer mould 1 is stationary and the central mould core 2 is moved during the moulding process.

Figure 10:
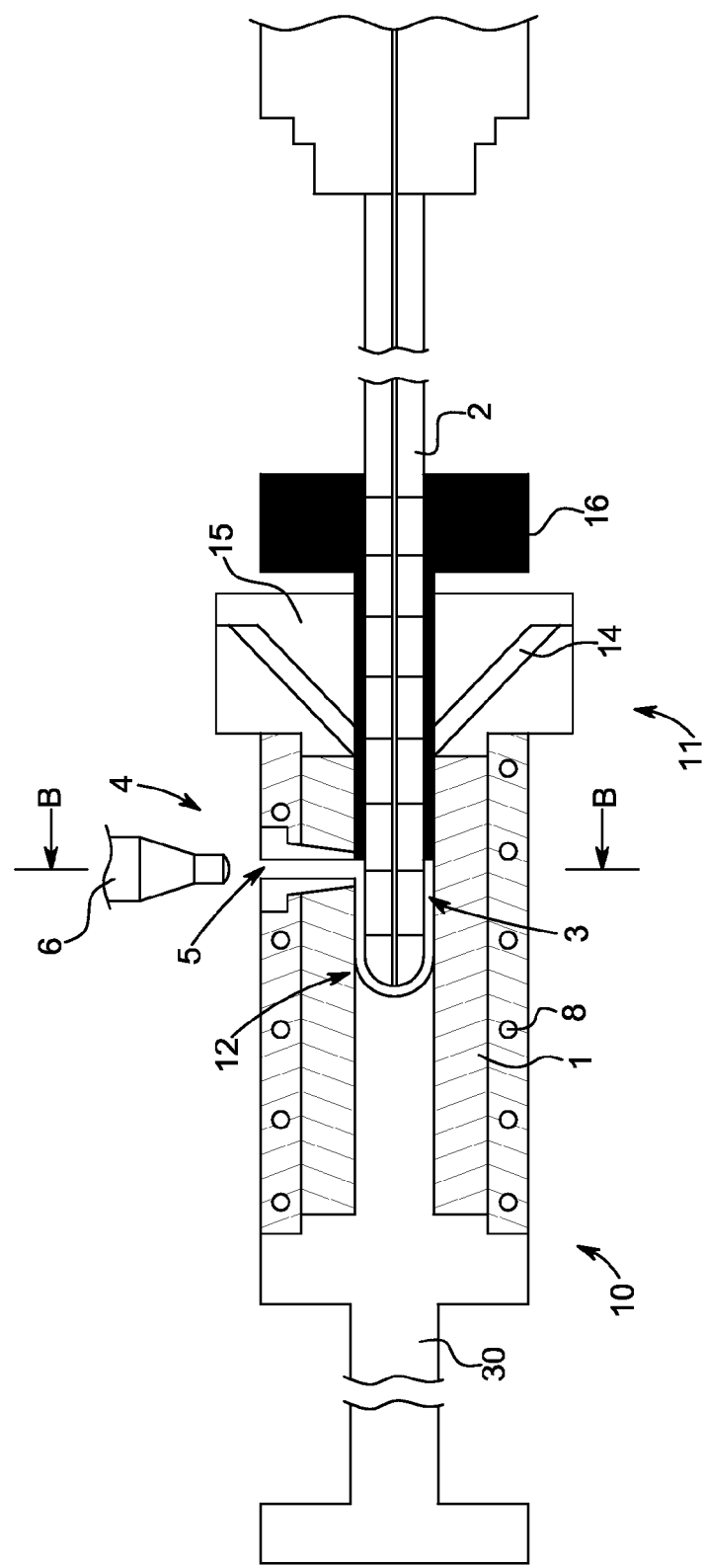
FIG. 10 is a schematic cross-sectional view of the initial position of the moulding apparatus according to a second embodiment of the disclosure.
Figure 11:
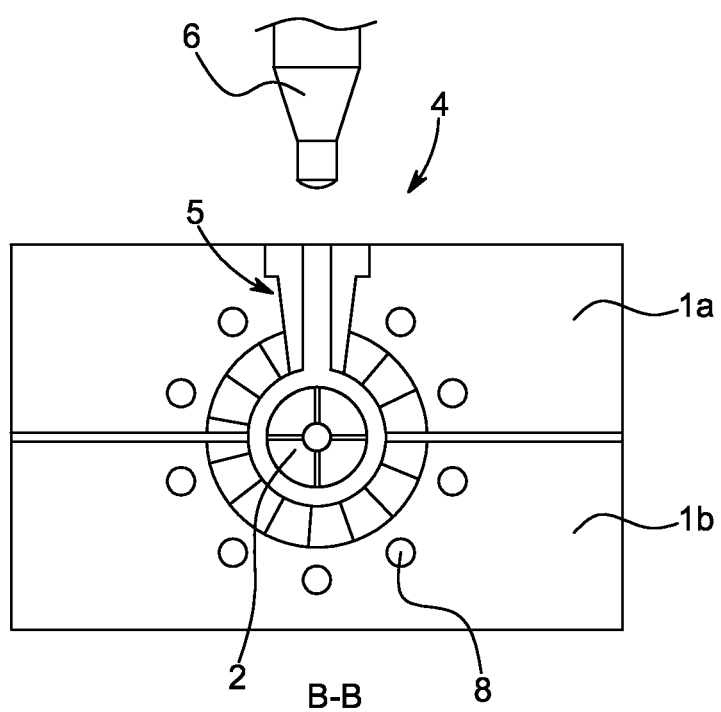
FIG. 11 is a cross-section along the section B-B of FIG. 10.

The initial position of the moulding apparatus is shown in FIG. 10, where the mould core 2 is retracted towards the second end 11 and the limiter piston 16 is positioned so that flow communication from the cavity 3 to the second end cavity 14 is blocked. In front of the tip end cavity 12 a movable tip mould piston 30 is provided which is movable together with the mould core 2 as the moulding process progresses. The inlet 4 is arranged as described above. The cross-section B-B in FIG. 10 of the moulding apparatus at the inlet 4 is also shown in FIG. 11.

Figure 12:
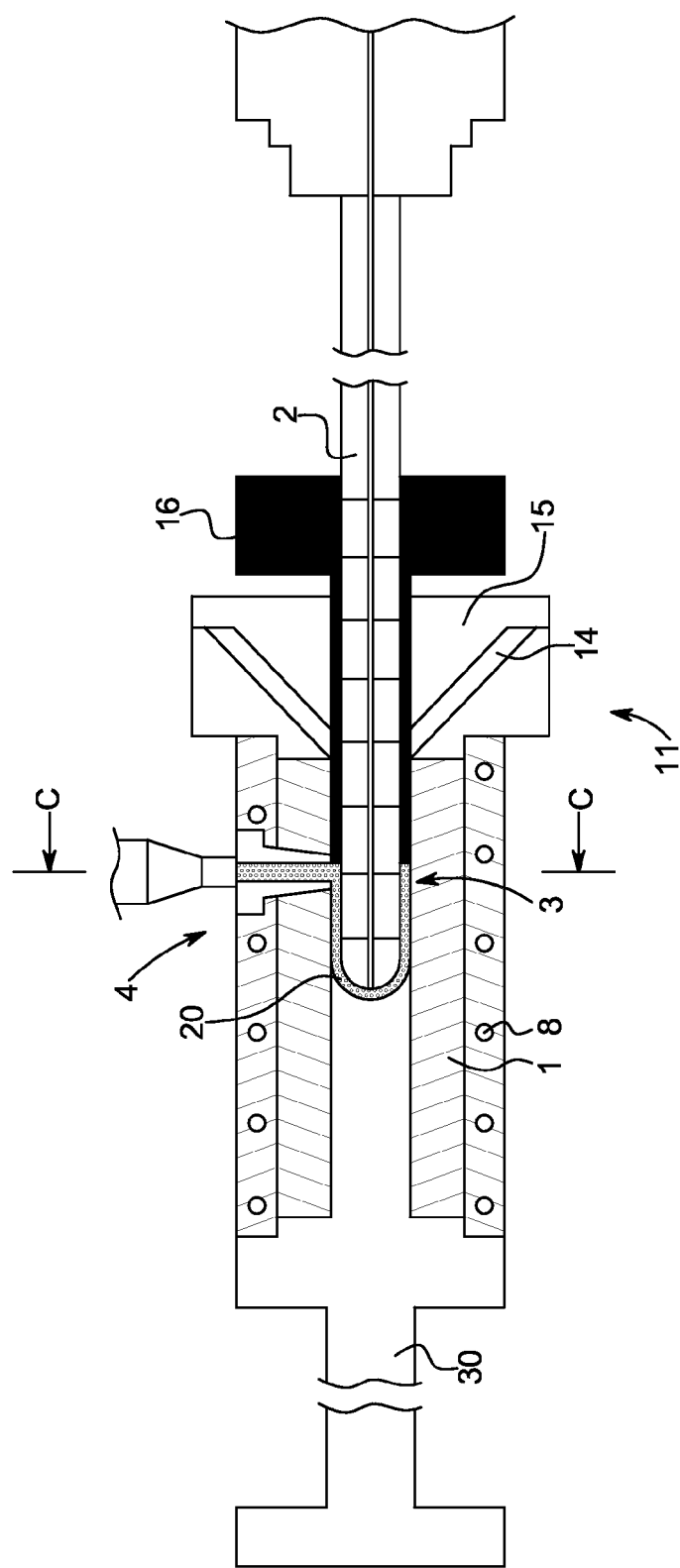
FIG. 12 is a schematic cross-sectional view of the start of the moulding apparatus.
Figure 13:
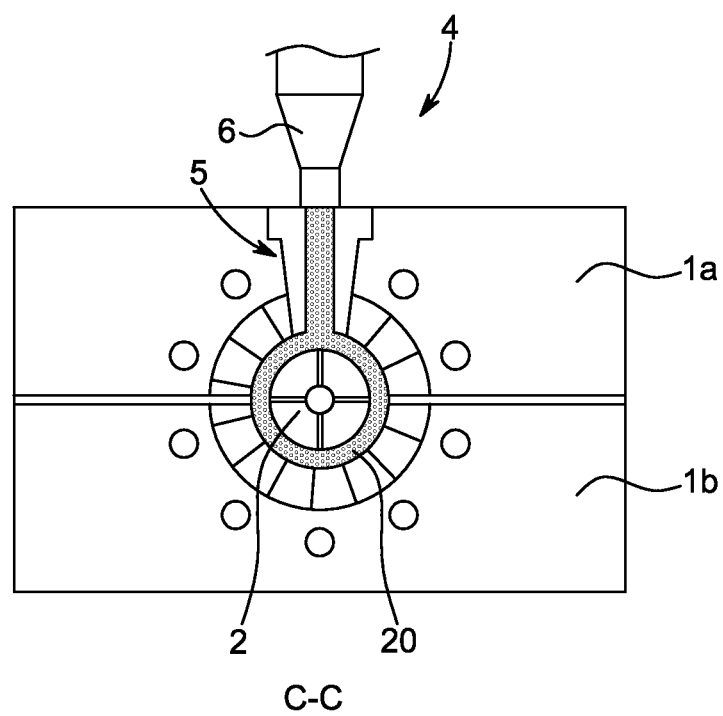
FIG. 13 is a cross-section along the section C-C of FIG. 12.
Figure 14:
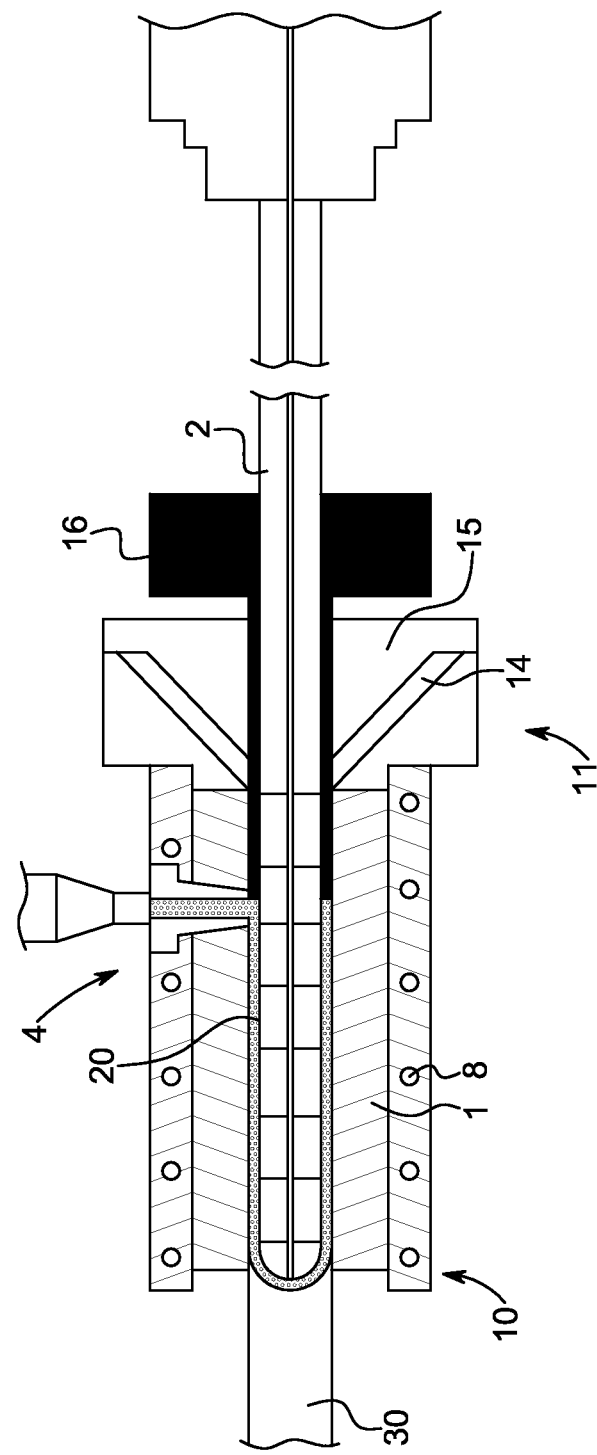
FIGS. 14 and 15 are schematic cross-sectional views of the moulding apparatus of FIGS. 10-13 during the moulding process.
Figure 15:
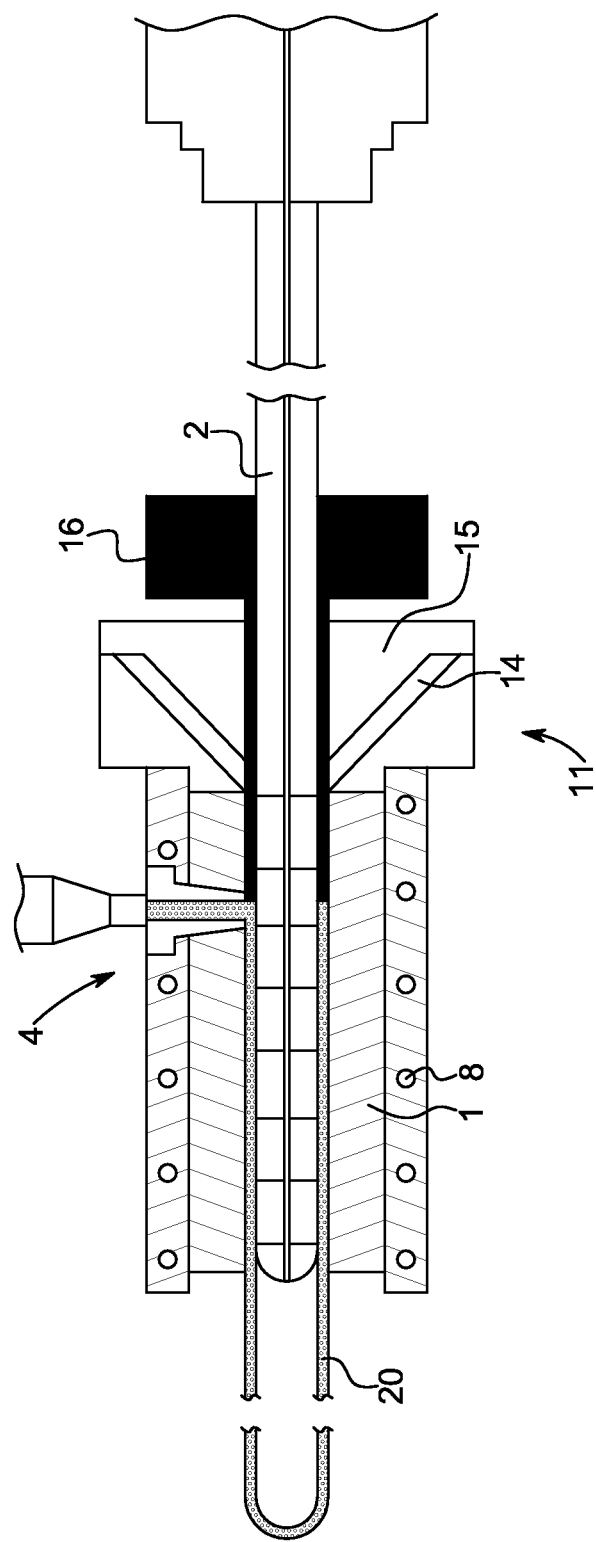
Figure 16:
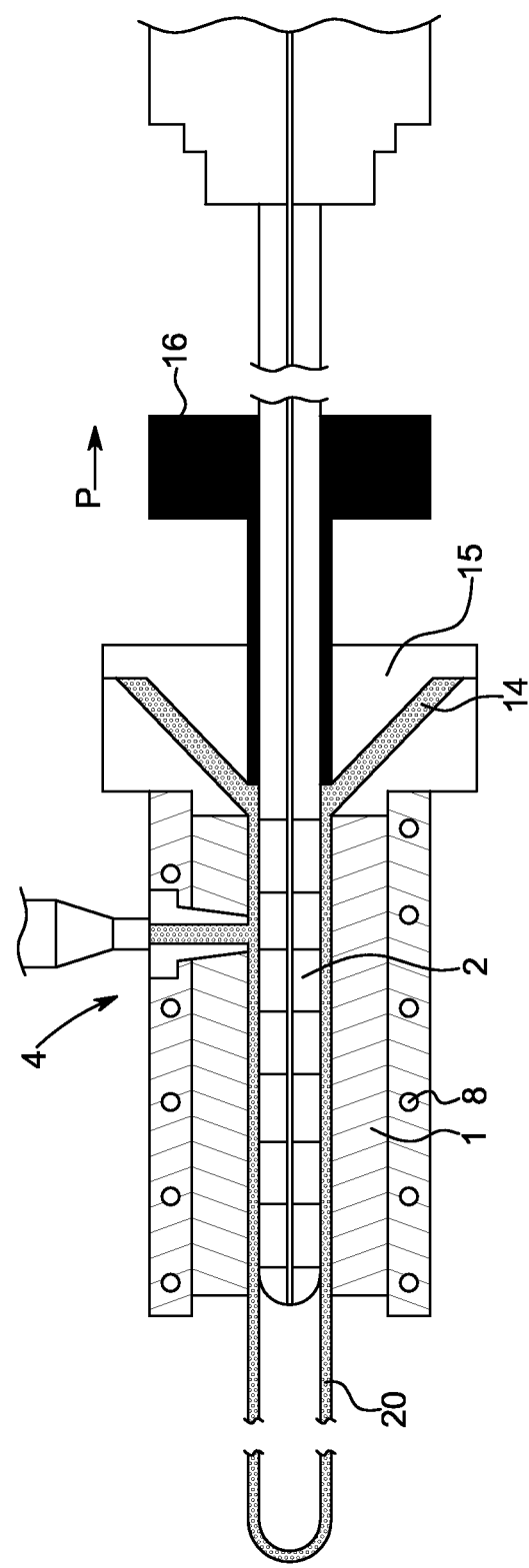
FIG. 16 is the moulding apparatus showing the moulding of the second end of the article.
Figure 17:
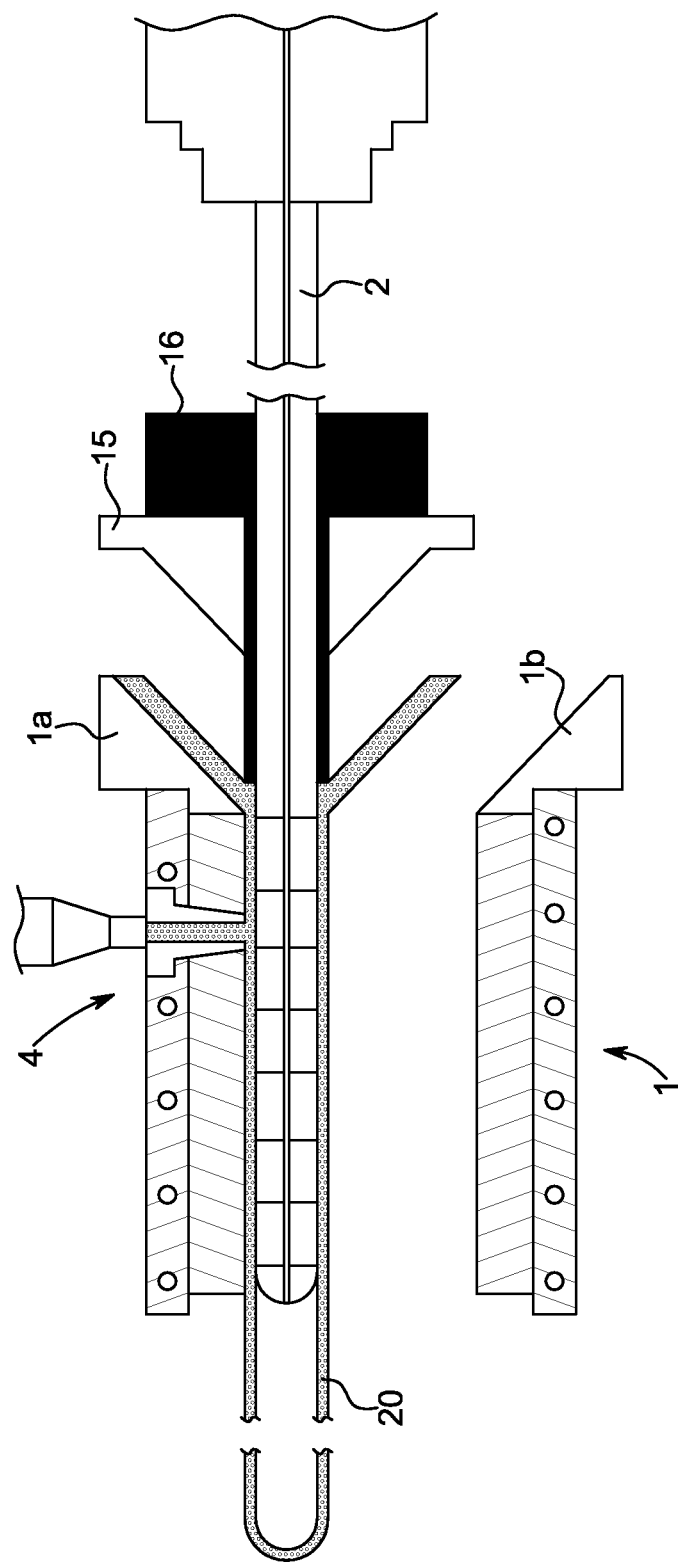
FIGS. 17 to 20 show a schematic cross-sectional view and a front cross-section of the moulding apparatus of FIGS. 10-16 during the step of ejecting the moulded article.
Figure 18:
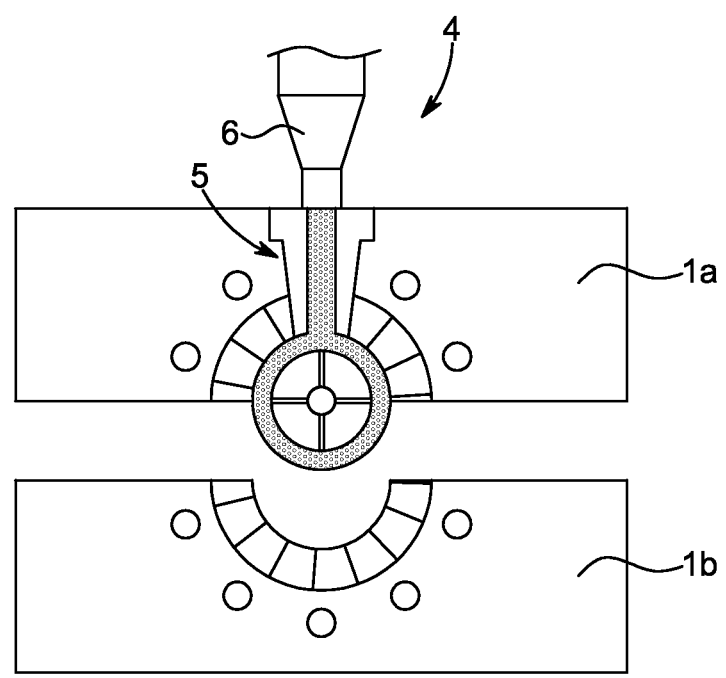
Figure 19:
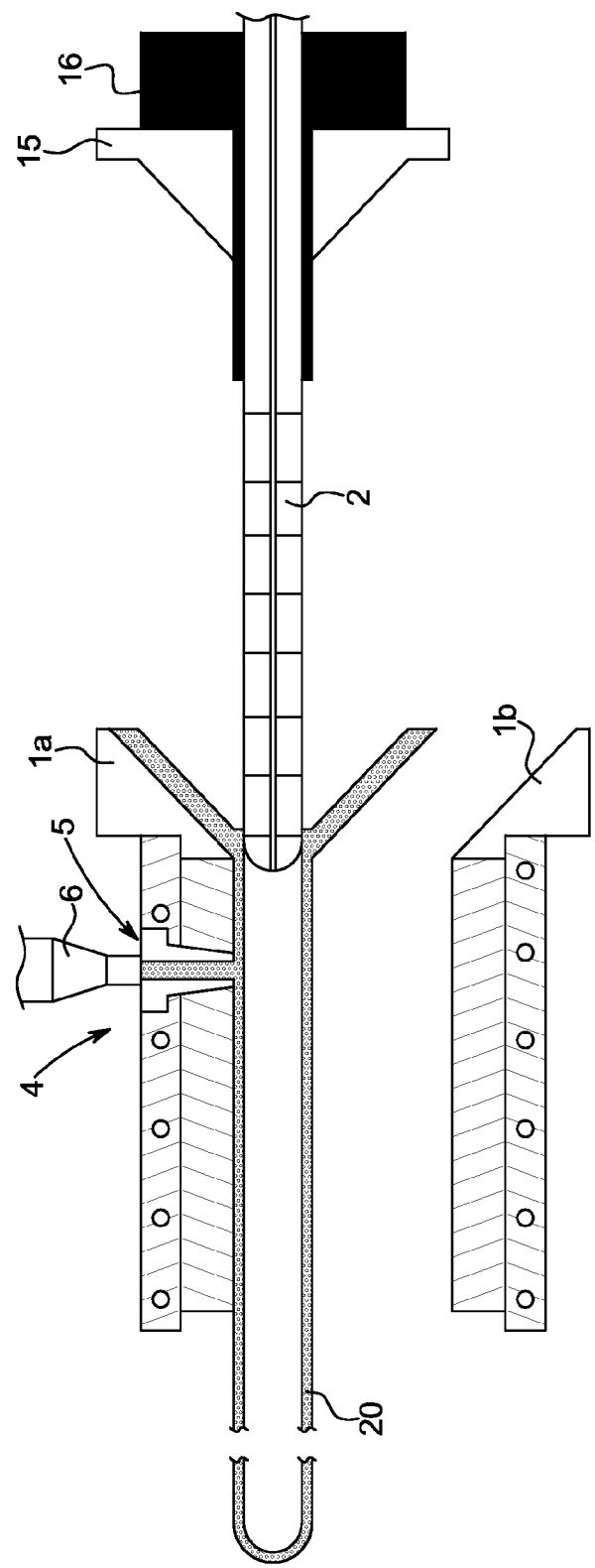
Figure 20:
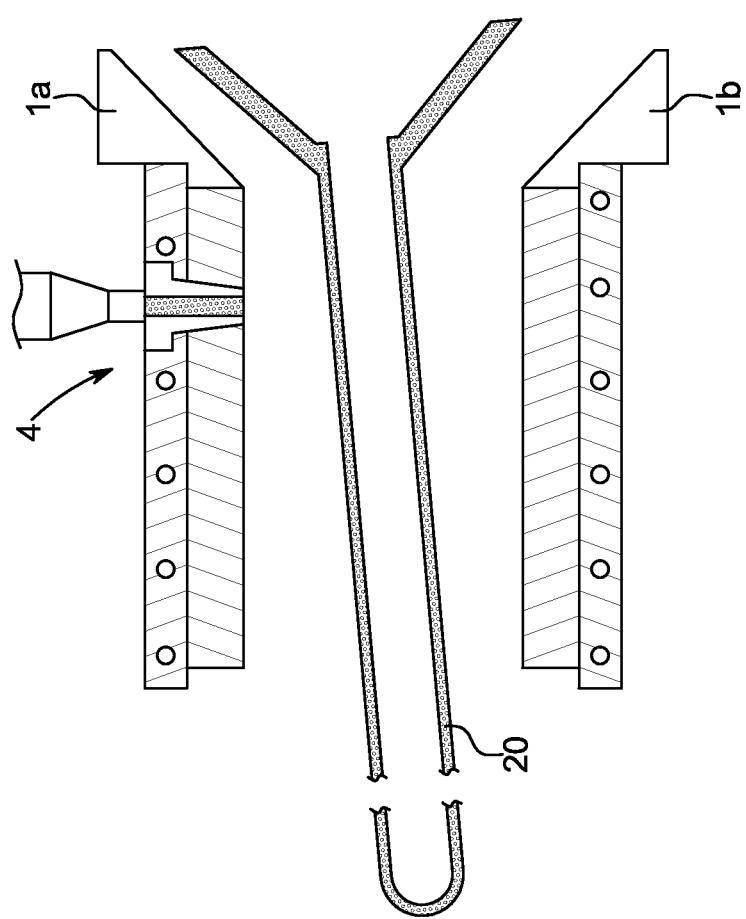

Liquidised moulding material 20 is advanced into the cavity 3 as shown in FIG. 12 and FIG. 13 as the moulding process starts. As shown in FIG. 14, the mould core 2 is advanced in the direction from the second end 11 to the first end 10 and the tip mould piston 30 is moved together with the mould core 2 until the desired length of the article is reached, as indicated at FIG. 15. When this final position is reached, the limiter piston 16 is retracted as shown by the arrow P in FIG. 16 whereby the liquidised moulding material flows into the second end cavity 14. When this cavity 14 is filled the moulding process is finished and the relevant parts of the moulding apparatus are detached, as shown in FIGS. 17 and 18. The outer mould 1 comprises an upper part 1a and a lower part 1b which are detached as well as the end moulding member 15 is retracted. Thereafter, the mould core 2 is retracted together with the end mould member 15 and the piston 16, as shown in FIG. 19 so that the article 20 is ejected from the mould as shown in FIG. 20.

This second embodiment is advantageous as the same mould can be used for manufacturing articles of different lengths without changing any of the components.

In short, the aspects of the first and second embodiments may be summarised in the following items:

An apparatus for injection moulding of an elongated hollow article, such as a urinary catheter, said apparatus comprising a mould comprising an elongated central mould core, an outer mould defining the outer peripheral surface of the article, wherein the mould core and the outer mould defines an elongated mould cavity having a first end and a second end and a tubular cavity section therebetween, where the first end is defining the first tip geometry of the article and the second end is defining the second tip end of the article; wherein said outer mould is provided with a track in which a movable inlet member having an inlet opening for the liquid moulding compound is slidably arranged; and wherein a movable limiter insert piston is provided in the cavity adapted to be retracted in the cylindrical cavity section from a first advanced position to a retracted position at the second end of the cavity so as to expand the cavity as the limiter insert piston is retracted and moulding compound is injected into the cavity.

the outer mould comprises two half parts which are detachable, such as an upper and a lower half part.

the inlet member is moving in the track of the split outer mould, preferably in the upper half part, from a first position near the first end section of the cavity to a second position near the second end section of the cavity.

the movable inlet member is provided with an annular cooling section downstream the inlet opening and a heated section upstream the inlet opening.

the inlet member is moving together with the mould core.

the limiter insert piston is moved together with the inlet member and the mould core until reaching its second end moulding position at the second end.

the outer mould is moving during the injection moulding and the central mould core is stationary until the moulding process is finished whereafter the mould core is retracted for ejection of the moulded component.

the cavity of the second end is provided with an outer peripheral surface defining an end geometry larger and the outer diameter of the cavity of the cylindrical section of said cavity.

the elongated mould core is provided with a fluid channel which is in flow communication with the first end of the mould cavity at the distal end mould core, and in connection with a fluid source and at the second end of the fluid channel.

the fluid channel is in flow connection with a pressurised air source providing air through the fluid channel.

the elongated hollow article is a catheter with the first end geometry being the proximal tip end of the catheter and the second end being the funnel-shaped connector end of the catheter.

at least a section of the inner surface of the outer mould is provided with a predetermined patterning for moulding such patterning on the surface of the article.

the tubular cavity is cylindrical with a circular cross-section.

A method of injection moulding of an elongated hollow article, such as a urinary catheter, said method comprising the steps of: injecting a liquidised moulding compound into a mould comprising an outer mould with a moveable inlet opening and an elongated mould core and an end limiter insert around the mould core defining an elongated mould cavity having a first end and a second end and an elongated tubular cavity section therebetween; moving the outer mould relative to the inlet opening and the elongated mould core and the limiter insert; at the second end retracting the limiter piston whereby the liquidised moulding compound fills the second end of the cavity; and then retracting the mould core and thereby ejecting the moulded article by opening the outer mould core.

the inlet member is moving in the track of the outer mould from a first position near the first end section of the cavity to a second position near the second end section of the cavity.

the movable inlet member is provided with an annular cooling section downstream the inlet opening and a heated section upstream the inlet opening.

the outer mould is moving during the injection moulding and the central mould core is stationary until the moulding process is finished whereafter the mould core is retracted for ejection of the moulded component.

the cavity of the second end is provided with an outer peripheral surface defining a geometry larger than the outer diameter of the cavity of the cylindrical section of said cavity.

the forming of the inside of the article is assisted by a supply of a fluid, such as pressurised air through a fluid channel exiting the tip of the mould core.

the elongated hollow article produced is a catheter with the first end geometry being the proximal tip end of the catheter and the second end being the funnel-shaped connector end of the catheter.

A urinary catheter having a proximal catheter tip portion, a distal connector portion, and a tubular portion therebetween, all portions being integrally formed by performing a method according to any of items mentioned above utilizing an apparatus of any of items mentioned above. Furthermore, at least a section of its outer surface of the distal tip portion and/or the tubular portion mould may be provided with a predetermined patterning.

Figure 21:
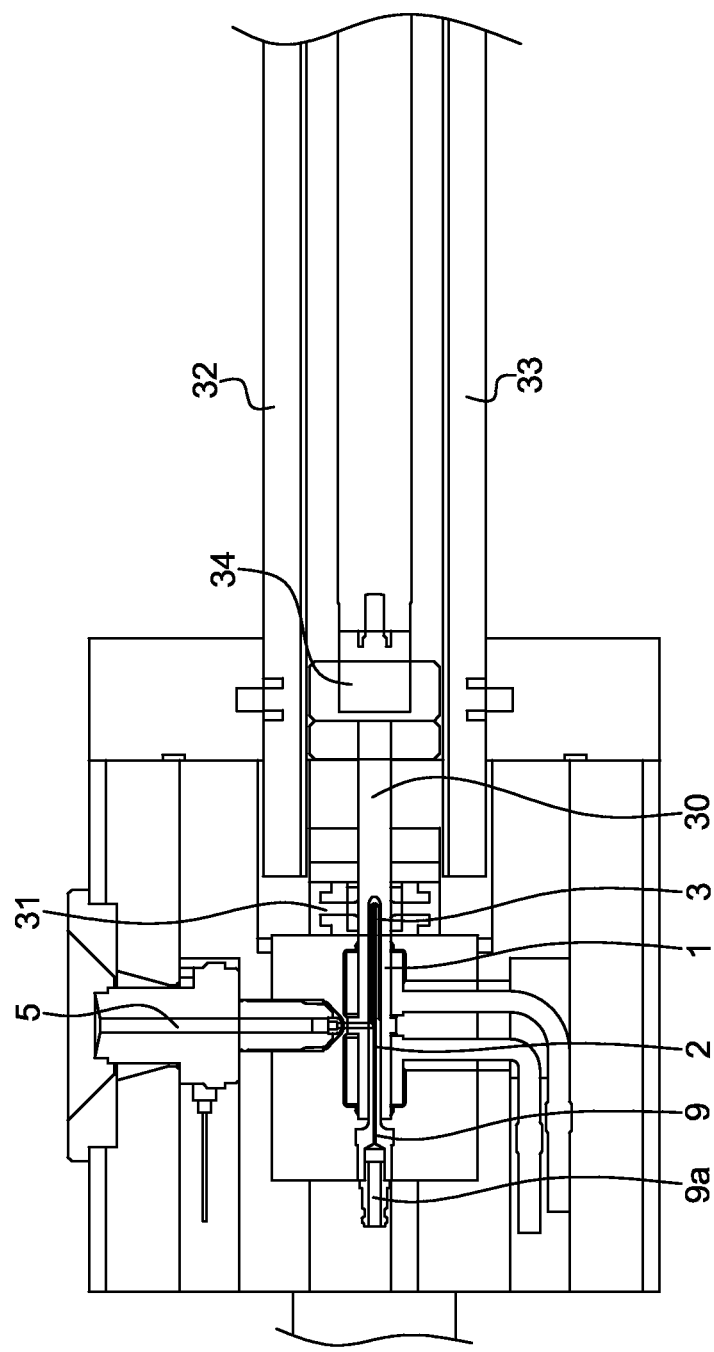
FIG. 21 is a schematic cross-sectional side view of a tool according to a third embodiment of the moulding apparatus in the initial position.
Figure 22:
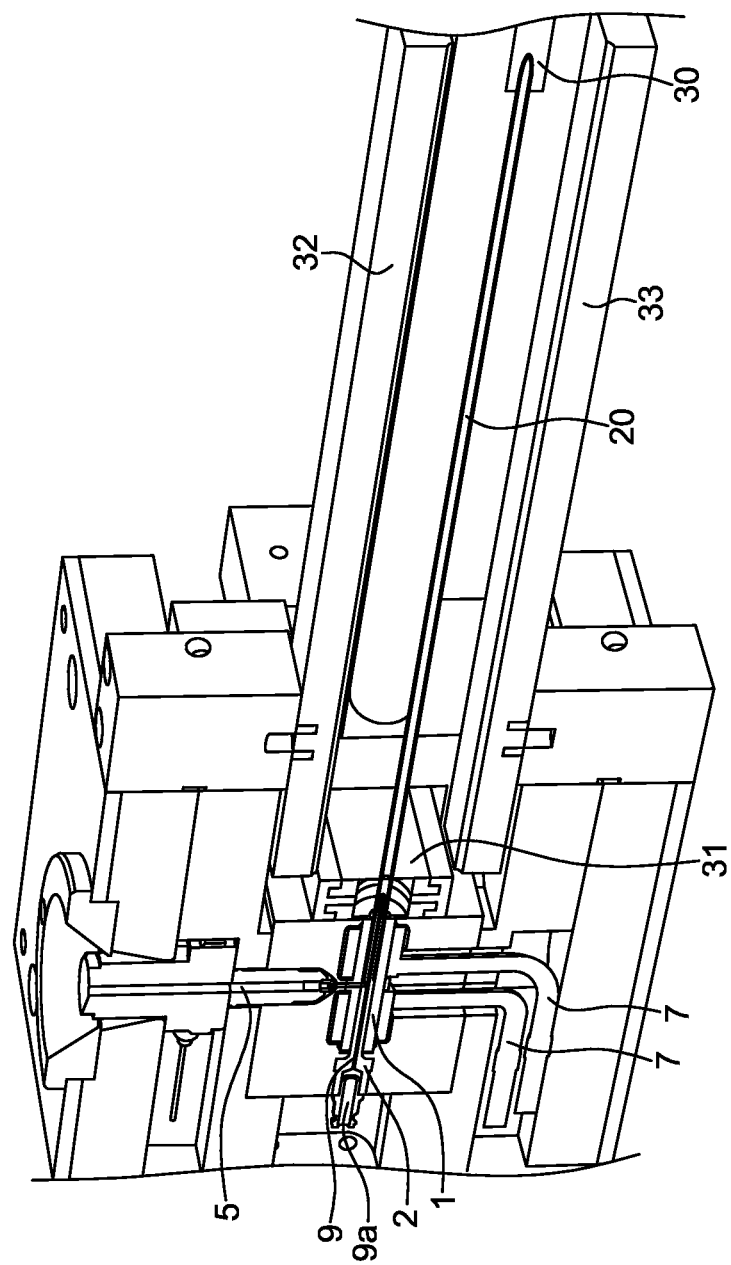
FIG. 22 is the tool in FIG. 21 in a perspective cross-sectional view during the moulding process.
Figure 23:
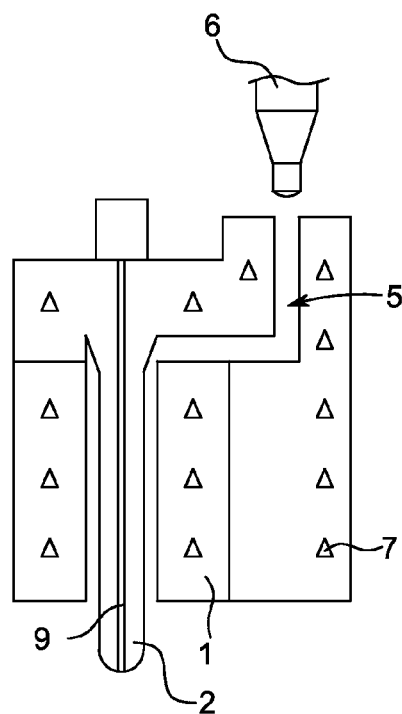
FIGS. 23-32 show the moulding process according to a third embodiment.
Figure 24:
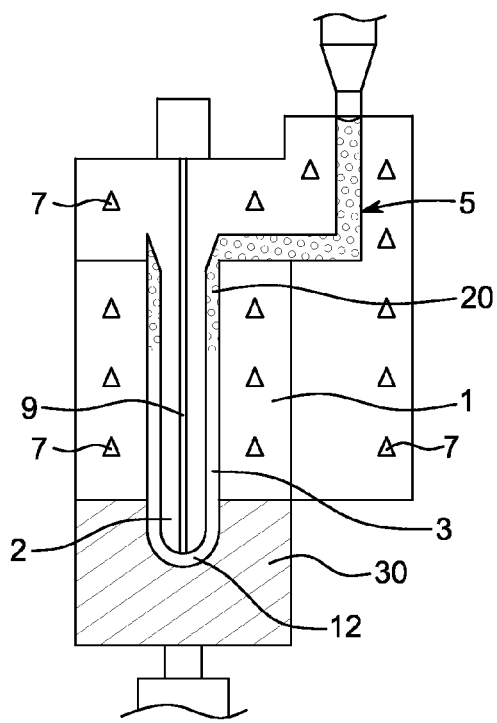

With reference to FIGS. 21-32, a third embodiment of a moulding apparatus is disclosed. In this embodiment, the cavity 3 is defined by a stationary outer mould 1 and the elongated mould core 2 which is also stationary. The cavity 3 is tubular in shape. In FIGS. 21 and 22 an example of a moulding apparatus according to the third embodiment is shown and the following FIGS. 23-32 the moulding sequence according to this third embodiment is shown step by step.

Figure 25:
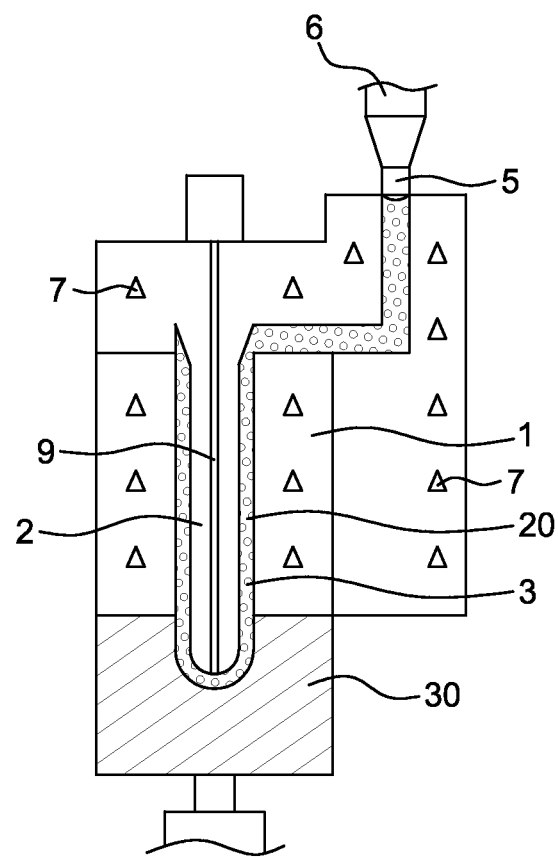
Figure 26:
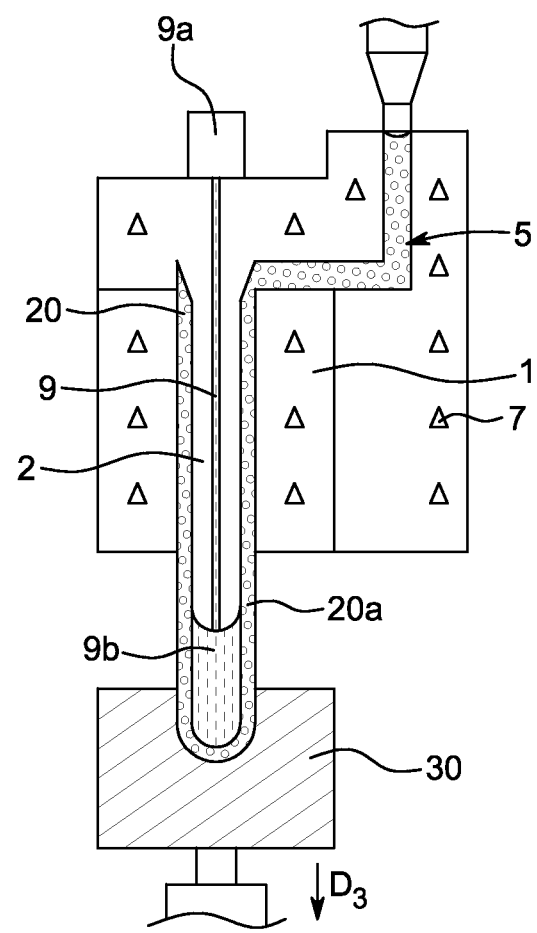

The elongated mould core 2 is provided with a central axial fluid channel 9 which is connected to a pressurised air supply 9a. The inlet 5 is provided substantially radially to the elongated mould core 2. The elongated mould core 2 is provided with an end section so that the extent of the cavity 3 is limited at the inlet 5 but extends beyond the outer mould 1 and into a tip mould 30. In the tip mould 30 there is provided a tip end cavity 12. The tip mould 30 is in its initial position positioned adjacent the outer mould 1 so that the tubular cavity 3 and the tip end cavity 12 are aligned and the tip of the elongated mould core 2 extends into the tip end cavity 12 (see FIG. 24). The outer mould 1 and the elongated mould core 2 are heated by having heating means 7 provided therein. The stationary mould members, i.e. the outer mould 1, the elongated mould core 2 and the inlet 5, are thereby kept heated to a temperature above the melting temperature of the moulding material, e.g. +175° C. for polyvinylchloride (PVC) or in the range of +200° C. to +350° C. for other polymer materials. At this initial stage of the moulding process, the cavity 3 is filled with moulding material 20 in accordance with a conventional injection moulding process. As the cavity 3 (including the tip end cavity 12) is filled, as shown in FIG. 25, the tip mould 30 starts moving in the direction D3, as shown in FIG. 26 and at the same time pressurised air is supplied from the pressurised air source 9a through the fluid channel 9 in the elongated mould core 2 and into the internal volume 9b of the moulded portion 20a of the product.

The tip mould 30 is kept cool, e.g. at +40° C. for PVC (and +20° C. to +130° C. for other polymers), i.e. well below the melting temperature of the polymer moulding material 20. The moulding material 20 is in a liquidised state in the heated section of the mould but is cooled and thereby solidifies as it leaves the heated mould members. The pressurised air supplied to the inside of the product formed stabilises the moulded portion 20a of the tubular product which is in the process of being moulded. The moulded portion 20a is thereby prevented from collapsing as it is pushed off the elongated mould core 2 by the liquidised moulding material 20, which is continuously being supplied under a predetermined pressure through the inlet 5. This pushing of the moulded product is also assisted by the supply of pressurised air 9a through the fluid channel 9 and into the inner volume 9b of the moulded portion 20a as well as the movement of the tip mould 30 which also assists the advancement of the moulded portion 20a off the elongated mould core 2. The tip mould 30 is arranged on a sledge 34 arranged for a linear movement in the direction D3.

Figure 27:
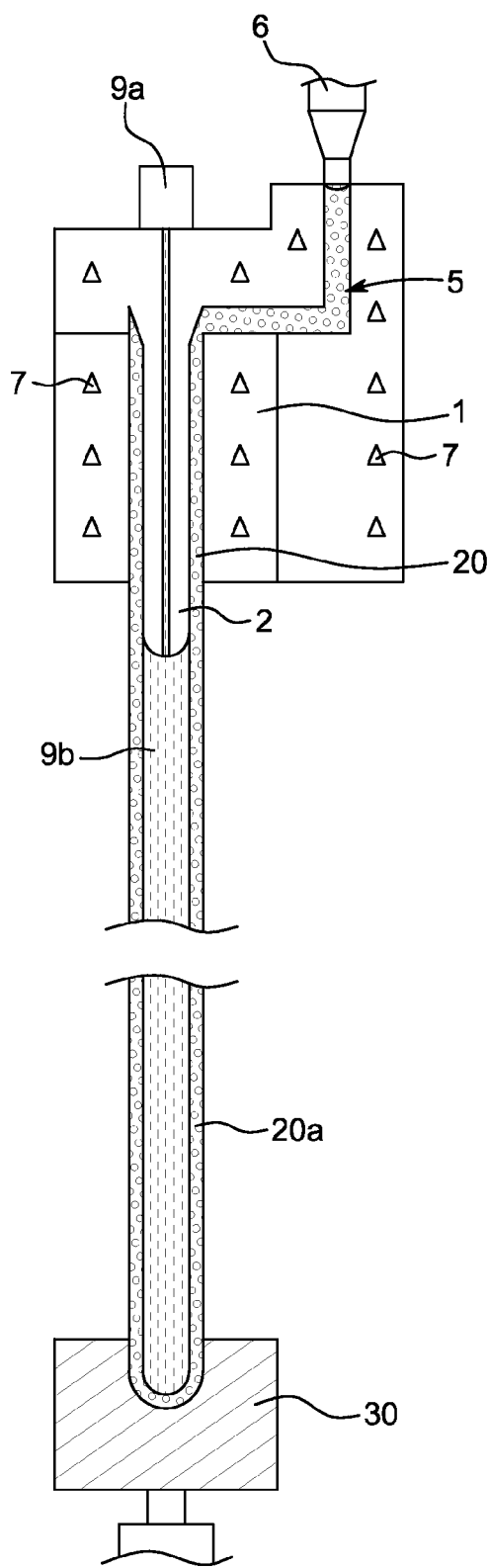
Figure 28:
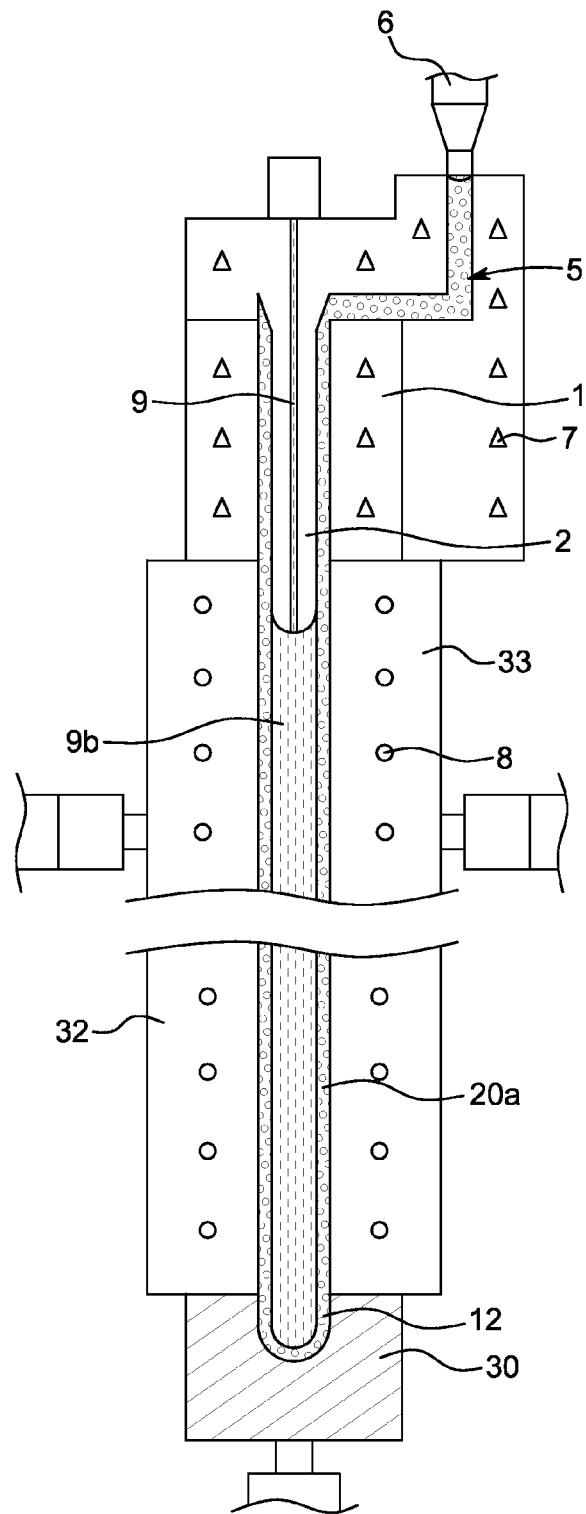
Figure 29:
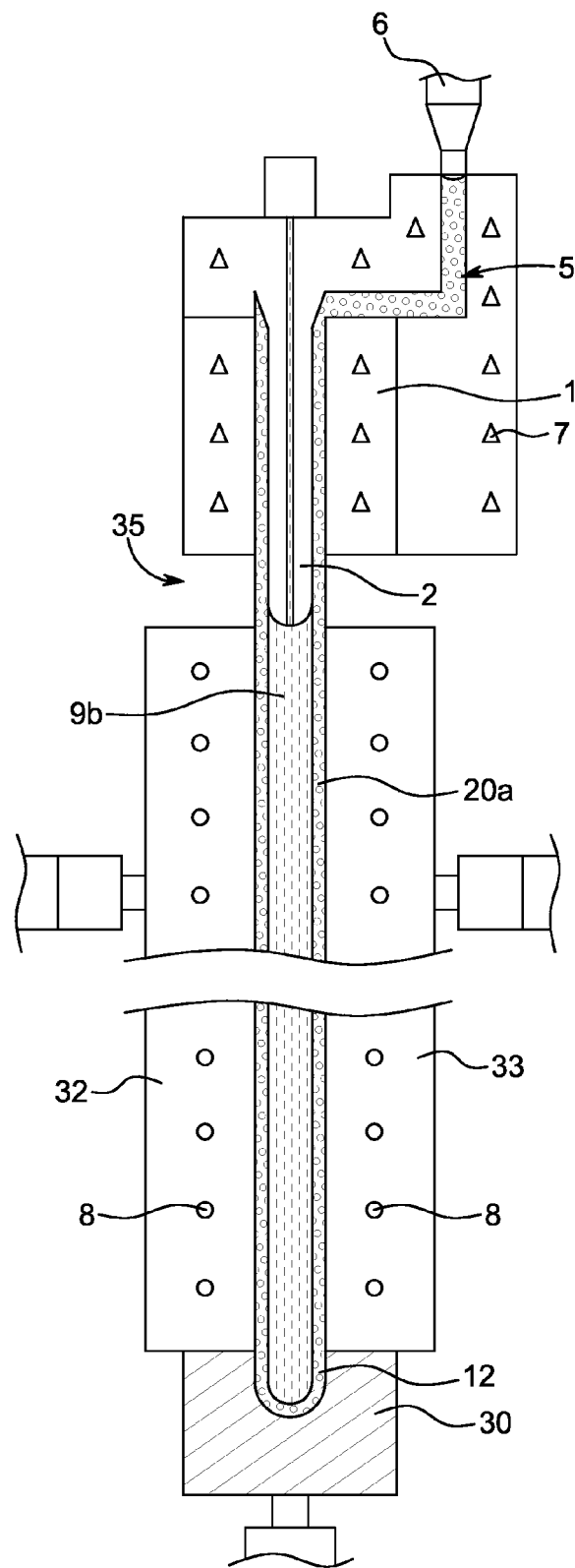

By this movement of the tip mould 30, the tubular form of the moulded portion is extended in length, as indicated in FIG. 27 by resembling a conventional extrusion process. This stage of the moulding process is also indicated in FIG. 22. As the required length of the tubular product is about to be reached, a set of cooling mould blocks 32, 33 are provided around the tubular moulded portion 20a to cool the product as shown in FIG. 28. With the cooling blocks 32, 33 clamped around the moulded product 20, as shown in FIG. 29, the moulding cycle is coming toward an end and the cooling blocks 32, 33 follow the movement of the tubular product 20a and creates a gap 35 between the cooling blocks 32, 33 and the mould 1. This cooling method is particularly suitable for materials sensitive to conventional cooling fluids, like water, oil, etc. A water bath can also be used to cool and solidify the part if needed.

Figure 30:
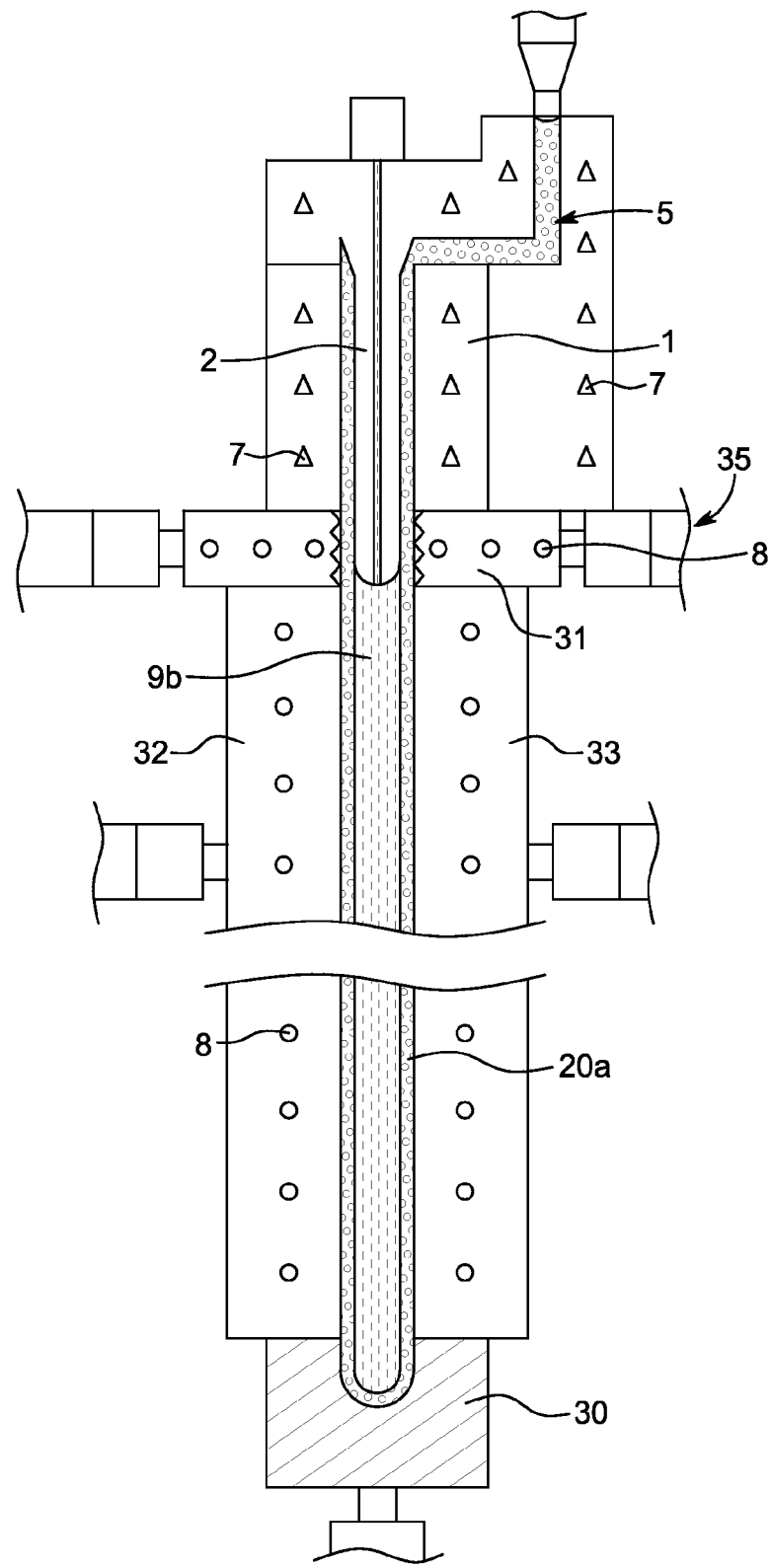

In this gap 35, a cutting arrangement 31 is then provided, as shown in FIG. 30. This cutting arrangement 31 preferably includes a set of knifes which in guillotine the tubular product and thereby cuts away the moulded product from the hot mould. As shown in FIG. 30, the cutting arrangement may preferably be provided with cooling means 8 so that the product is cooled when the cutting arrangement 31 is moved into its active position.

Figure 31:
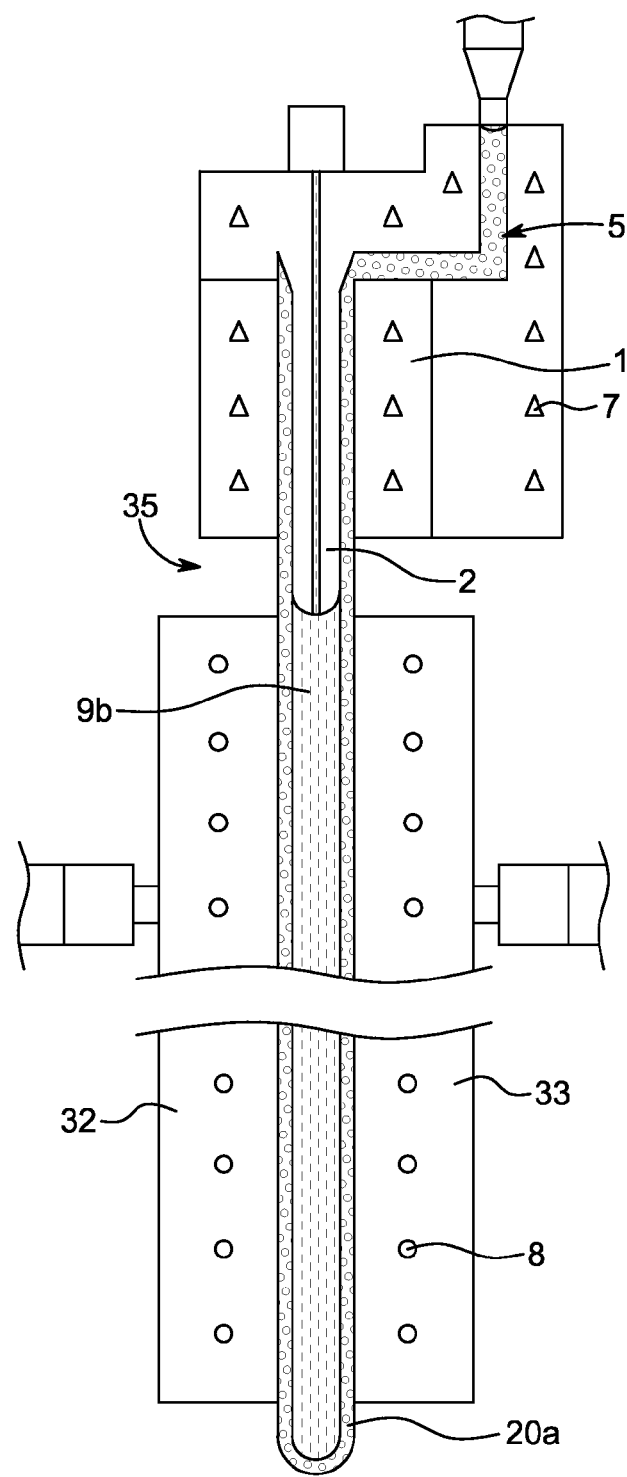
Figure 32:
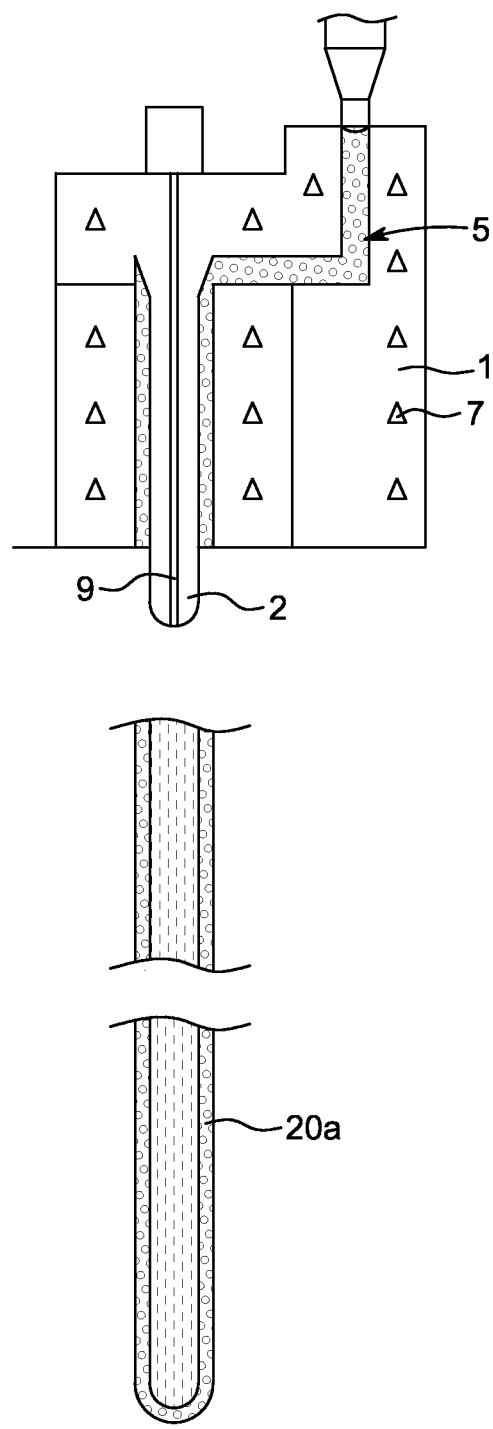

When the product has been cut, the cutting arrangement 31 is removed and the tip mould 30 is then moved further whereby the product 20a is held between the two cooling mould blocks 32, 33, as shown in FIG. 31. The product is thereafter freed as shown in FIG. 32, and the moulding cycle can continue over again as in FIG. 24 where the tip mould 30 is returned to its initial position abutting the outer mould 1 around the elongated mould core 2.

Although not shown in the figures, it is realised that the cooling mould blocks 32, 33 may be formed with a funnel cavity at the mould facing end so that when the mould blocks 32, 33 are clamped around the tubular moulded product as shown in FIG. 29, the pressurised air being supplied from the fluid passage 9 of the elongated mould core 2 may be utilised to blow moulding a funnel shape or another predetermined end geometry in the product prior to the cutting action at the stage illustrated in FIG. 30. The predetermined geometry of the hollow article may also comprise an oval shape at specific sections of the tube, or a structured outer surface pattern of the tube or parts of the tube, such as a honey comb pattern or the like.

FIGS. 33 to 43 show a moulding cycle according to a fourth embodiment of the disclosure. The moulding apparatus and method is similar to the third embodiment, but instead of a stationary elongated mould core, a moveable elongated mould core 2, 2', 2" is used.

Figure 33:
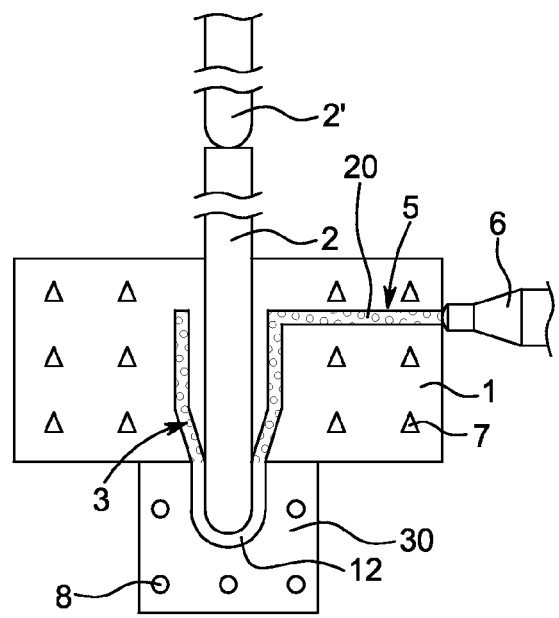
FIGS. 33-43 show the moulding process according to a fourth embodiment.
Figure 34:
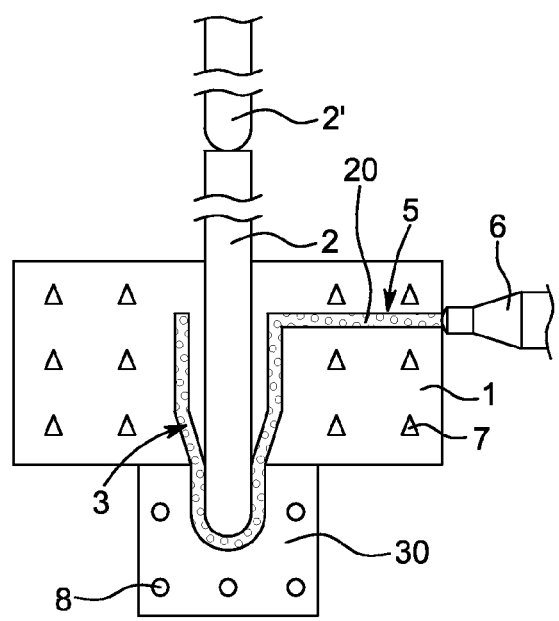
Figure 35:
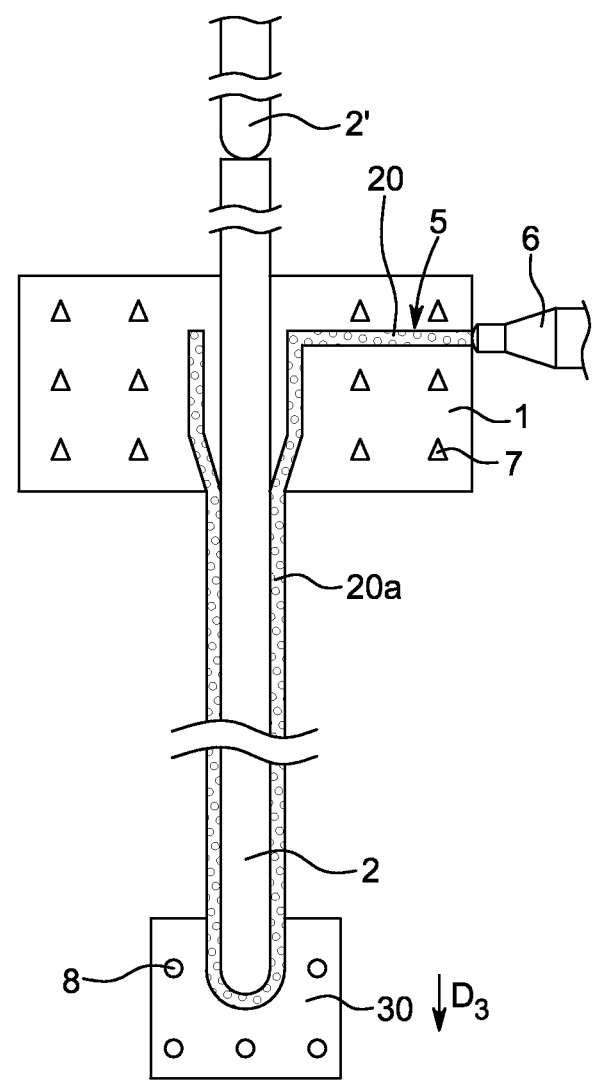
Figure 36:
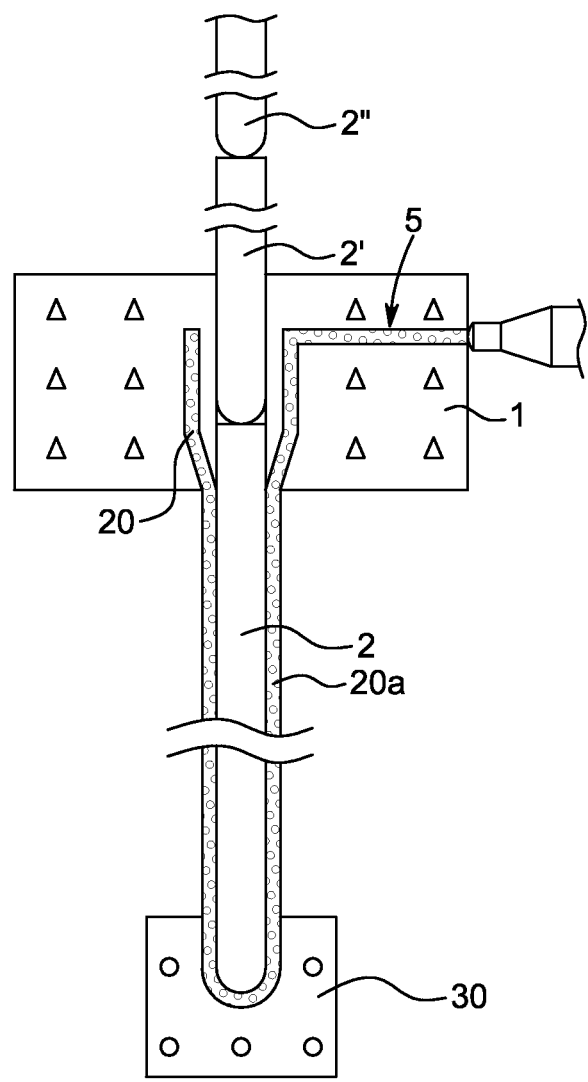

The central mould 1 is provided with an inlet 5 which is provided substantially radially to the elongated mould core 2 and through which inlet 5 the liquidised moulding material 6 is fed. The elongated mould core 2 is provided with an end section so that the extent of the cavity 3 is limited at the inlet 5 but extends beyond the outer mould 1 and into a tip mould part 30. In the tip mould part 30 there is provided a tip end cavity 12. The tip mould part 30 is shown in FIG. 33 in its initial position positioned adjacent the outer mould 1 so that the tubular cavity 3 and the tip end cavity 12 are aligned and the tip of the elongated mould core 2 extends into the tip end cavity 12. The outer mould 1 is heated by having heating means 7 provided therein and is kept heated to a temperature above the melting temperature of the moulding material, e.g. +175° C. for polyvinylchloride (PVC) or in the range of +200° C. to +350° C. for other polymer materials. At this initial stage of the moulding process, the cavity 3 is filled with moulding material 20 in accordance with a conventional injection moulding process. As the cavity 3 (including the tip end cavity 12) is filled, as shown in FIG. 34, the tip mould 30 starts moving in the direction D3, as shown in FIG. 35 and at the same speed of movement, the elongated mould core 2 is being pushed out of the central mould 1 so it follows the moulded portion 20a of the product. The elongated mould core 2 follows the product and is pushed through the central mould 1 by a second elongated mould core 2' which eventually is positioned in the mould for starting the next moulding cycle (see FIG. 43).

The tip mould part 30 is kept cool, e.g. at +40° C. for PVC (and +20° C. to +130° C. for other polymers), i.e. well below the melting temperature of the polymer moulding material 20. The moulding material 20 is in a liquidised state in the heated section of the mould but is cooled and thereby solidifies as it leaves the heated mould 1. The moulded portion 20a is prevented from collapsing as it is supported by the elongated mould core 2.

Figure 37:
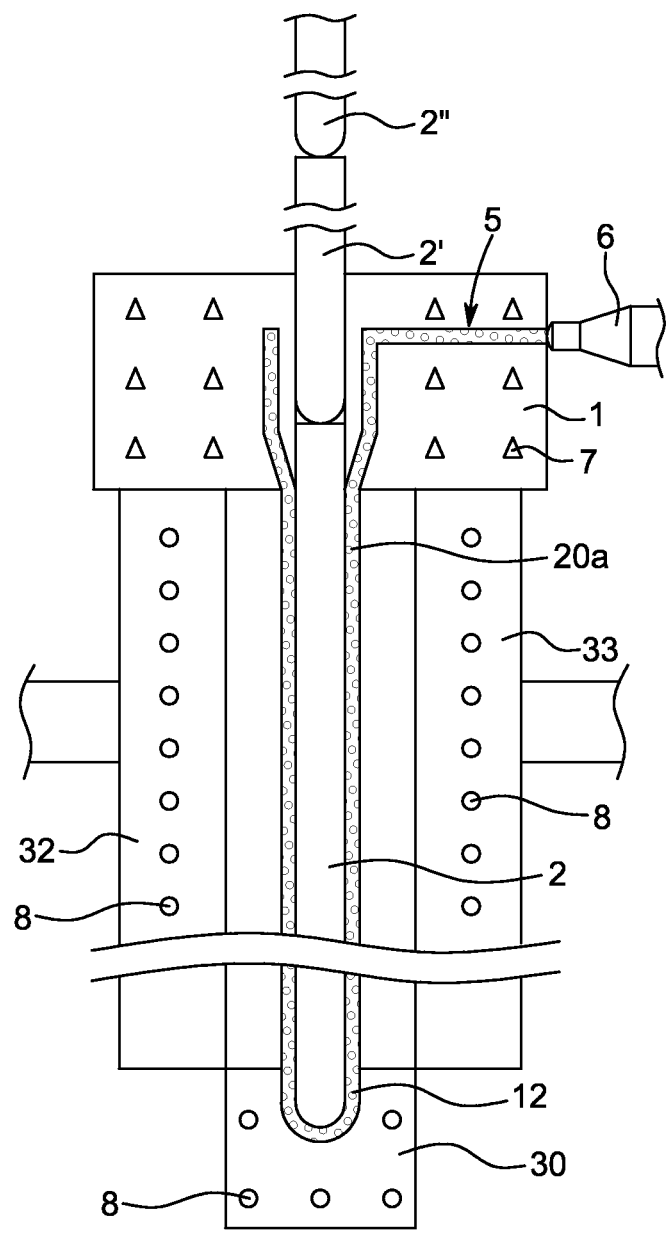
Figure 38:
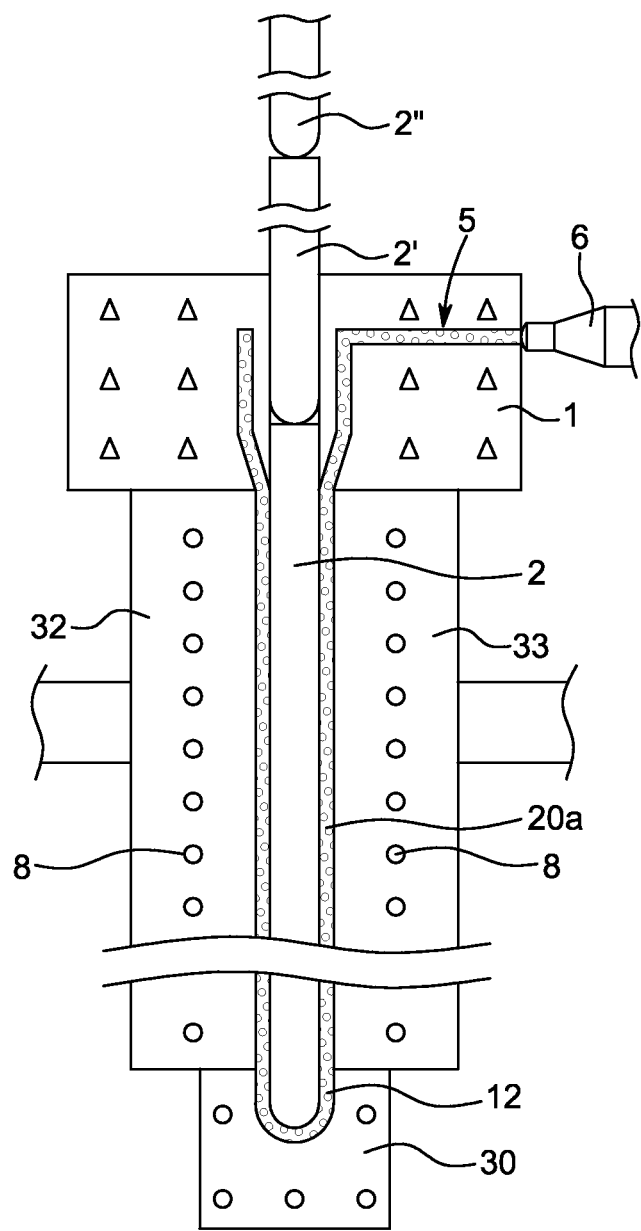
Figure 39:
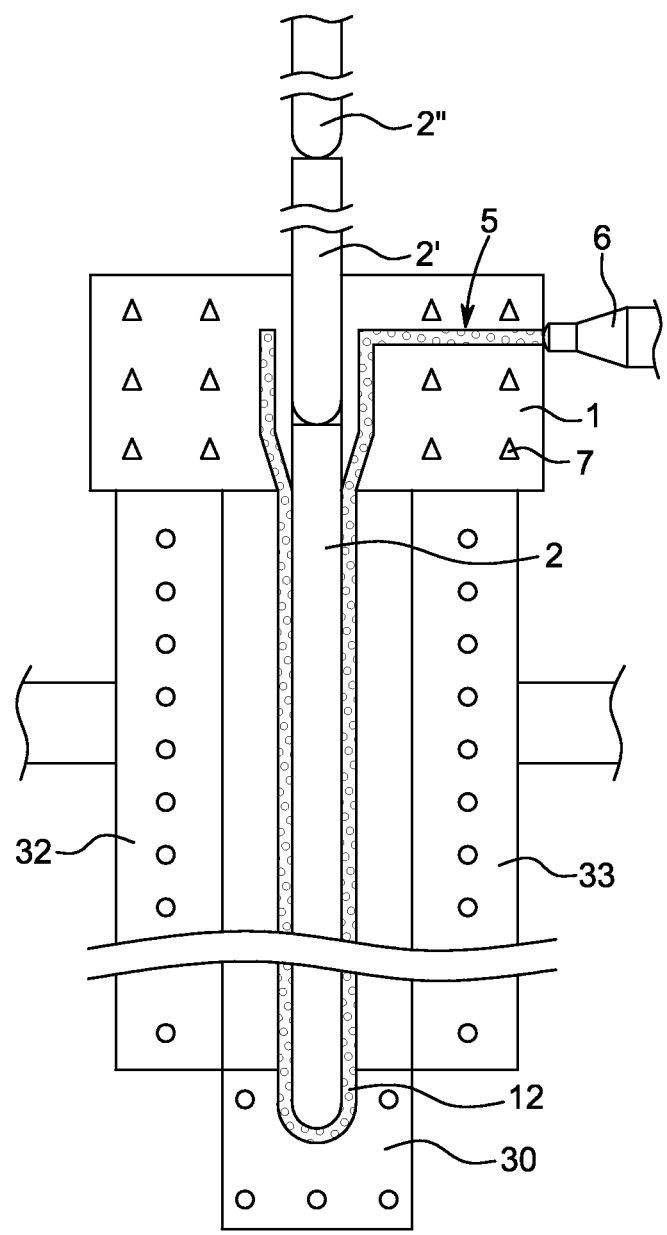
Figure 40:
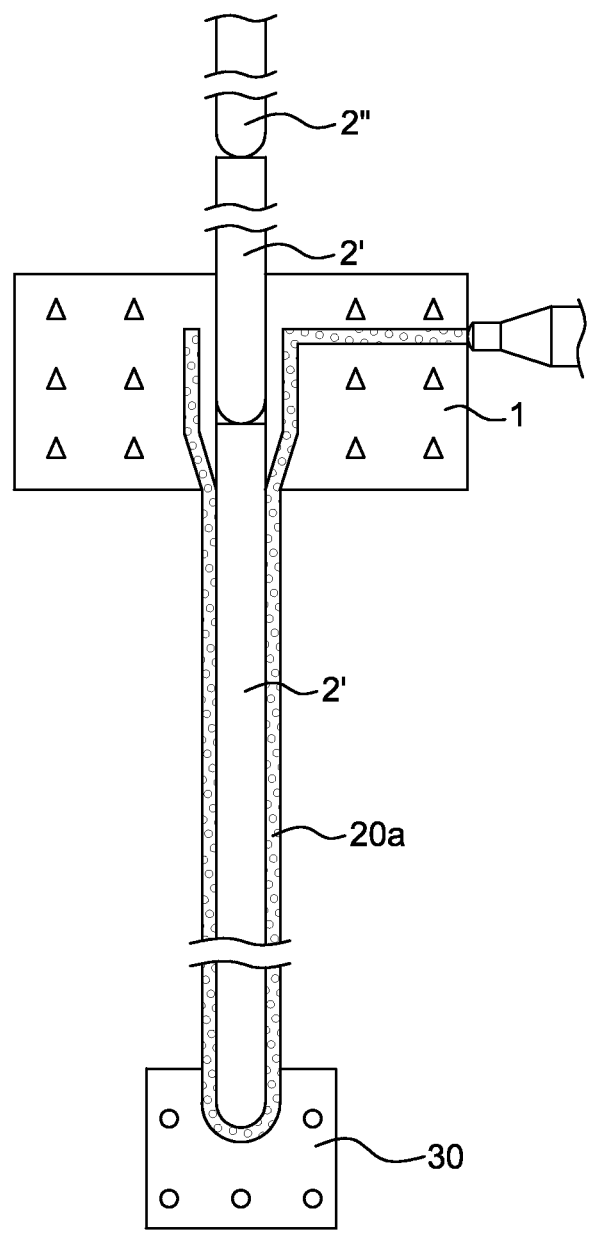

As the required length of the tubular product is reached (see FIG. 36), a set of cooling mould blocks 32, 33 are provided around the tubular moulded portion 20a to cool the product as shown in FIG. 37. With the cooling blocks 32, 33 clamped around the moulded product 20, as shown in FIG. 38, and thereafter the cooling blocks 32, 33 are retracted again when the product is cooled (see FIGS. 39 and 40).

Figure 41:
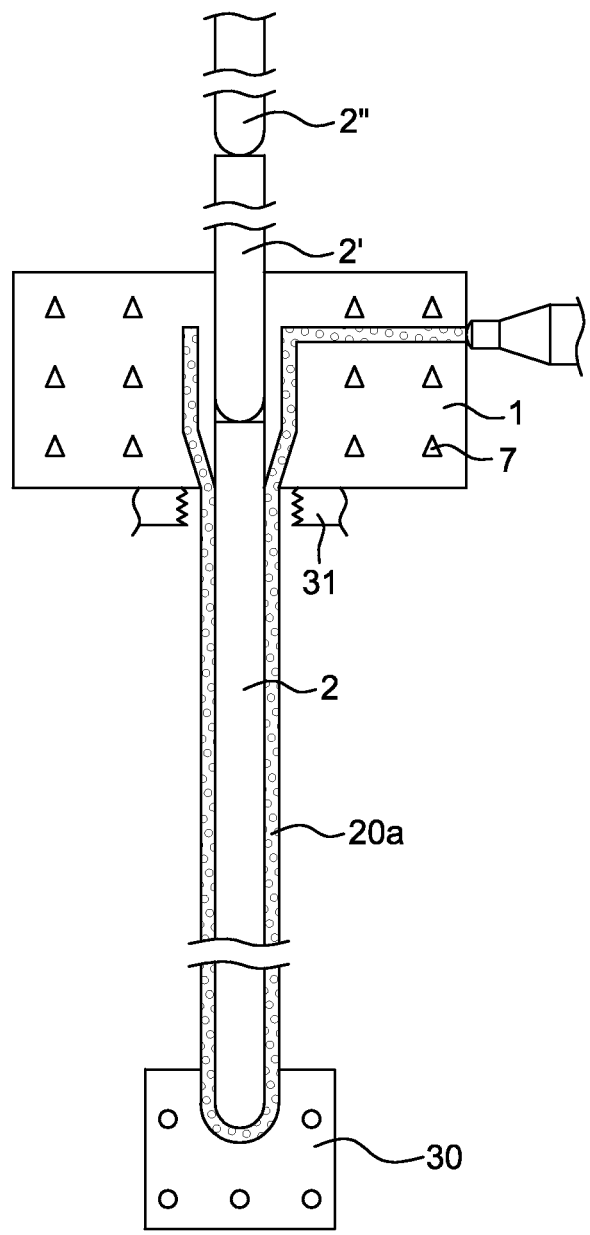
Figure 42:
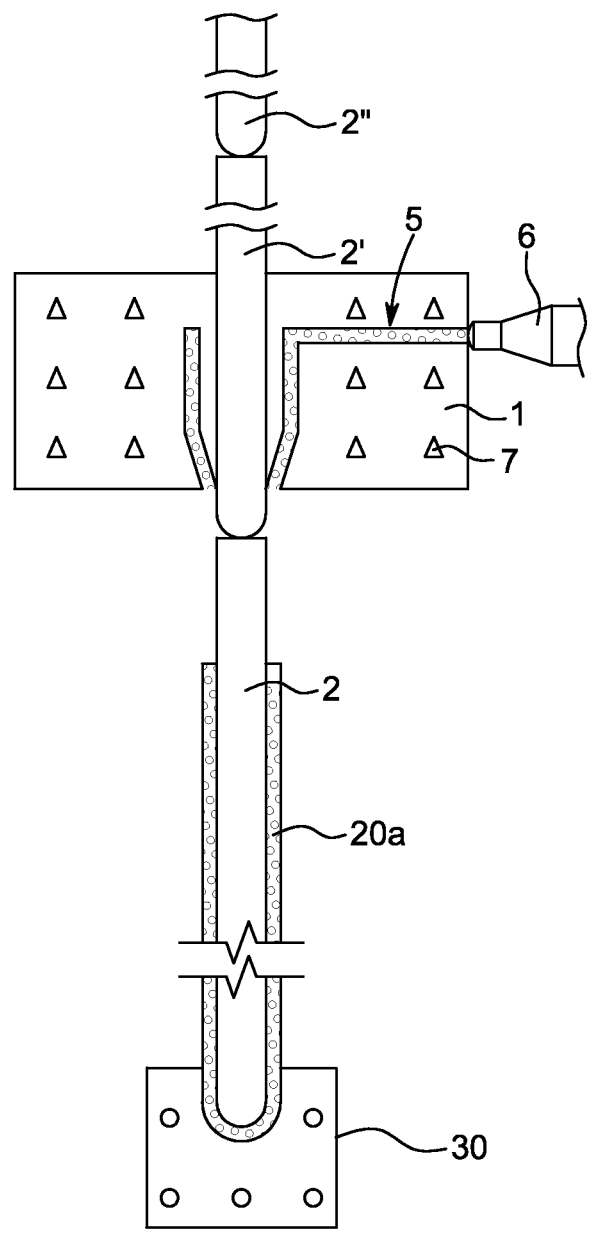
Figure 43:
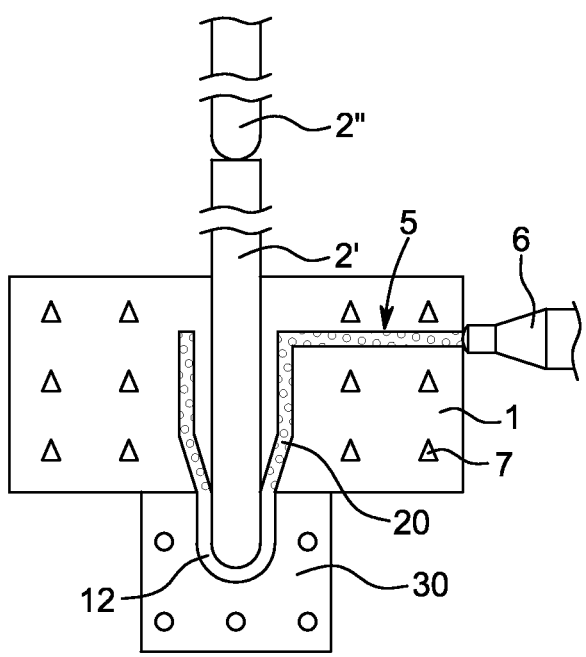

As shown in FIG. 41, a cutting arrangement 31 is moved into its active position to cut off the moulded product from the central mould 1. When the product has been cut off, the cutting arrangement 31 is removed and the tip mould 30 is then moved further and the elongated mould core 2 is pushed out of the central mould 1, whereby the product 20a can be freed as shown in FIG. 42, and the moulding cycle can continue over again as in FIG. 43 where the tip mould 30 is returned to its initial position abutting the outer mould 1 around the elongated mould core 2.

The invention claimed is:
1. A method of injection moulding of an elongated hollow article, said method comprising the steps of:
    injecting a liquidized moulding compound into a mould comprising a heated central mould with an inlet opening for entering the liquidized moulding compound into a substantially tubular cavity formed in said central mould, said mould further comprising an elongated central mould core which is provided in the tubular cavity and extending beyond said tubular cavity and into a tip mould cavity of a tip mould part which is aligned with the tubular mould cavity in the longitudinal axis of the central mould core;

moving, once the tip mould cavity is filled, the tip mould part in a linear direction along the longitudinal axis of the central mould core from a first position where the tip mould part is abutting the central mould to a second position at a predetermined distance from said first position via a sledge;

encompassing and clamping the moulded portion of the article with mould blocks with end contacting surfaces having an end section geometry when the tip mould is approaching said second position; and supplying pressurized air within the moulded portion of the article to blow mould said end section geometry, whereby said elongated central mould core is stationary and provided with a fluid channel which is in flow communication with the tip mould cavity at the distal end elongated central mould core, and in connection with the pressurized air at a second end of the fluid channel.

2. A method according to claim 1, further comprising the step of cooling the hollow article when the tip mould part has reached the second position.

3. A method according to claim 1, wherein the mould blocks are provided with inner contacting surfaces resembling the shape of the tubular mould cavity.

4. A method according to claim 1, whereby the fluid channel is in controlled flow connection with a pressurized air source providing pressurized air through the fluid channel into the inner volume of the moulded article during the movement of the tip mould part between the first position to the second position.

5. A method according to claim 1, including controlling the temperature of the elongated central mould core for maintaining an elevated temperature similar to that of the heated central mould.

6. A method according to claim 1, including controlling the temperature of the movable tip mould part for maintaining a temperature lower than of that the heated central mould.

7. A method according to claim 1, including controlling the temperature of the heated central mould for maintaining an elevated temperature at which the moulding compound is kept liquidized.

8. A method of injection moulding of an elongated hollow article, said method comprising the steps of:
injecting a liquidized moulding compound into a mould comprising a heated central mould with an inlet opening for entering the liquidized moulding compound into a substantially tubular cavity formed in said central mould, said mould further comprising an elongated central mould core which is provided in the tubular cavity and extending beyond said tubular cavity and into a tip mould cavity of a tip mould part which is aligned with the tubular mould cavity in the longitudinal axis of the central mould core;

moving, once the tip mould cavity is filled, the tip mould part in a linear direction along the longitudinal axis of the central mould core from a first position where the tip mould part is abutting the central mould to a second position at a predetermined distance from said first position via a sledge; and cooling the hollow article when the tip mould part has reached the second position whereby the cooling is performed by a set of cooling mould blocks which are provided for encompassing and clamping the moulded portion of the article by radially inward movement when the tip mould is approaching said second position, wherein the cooling mould blocks are provided with inner contacting surfaces resembling the shape of the tubular mould cavity.

9. A method according to claim 8, whereby the moulded article is cut away from the mould by cutting means provided in a gap between the cooling blocks and the outer mould is provided at the second position.

10. An apparatus for injection moulding of an elongated hollow article, said apparatus comprising:
a heated central mould with an inlet opening for entering liquid moulding compound into a substantially tubular cavity formed in said central mould;

an elongated central mould core which is provided in the tubular cavity that extends beyond said tubular cavity and into a tip mould cavity of a tip mould part which is aligned with the tubular mould cavity in the longitudinal axis of the central mould core, wherein the tip mould part is moveable in a linear movement in a direction along the longitudinal axis of the elongated central mould core; and a set of mould blocks are provided for encompassing and clamping the moulded portion of the article when the tip mould is approaching said second position, the moulding blocks being formed with end contacting surfaces having an end section geometry, wherein the elongated central mould core has a fluid channel in flow communication with the tip mould cavity and a pressurized air source supplying pressurized air to blow mould the end geometry into the elongated hollow article, wherein the elongated central mould core is stationary and the fluid channel is in flow communication with the tip mould cavity at the distal end of the elongated central mould core, and in connection with the pressurized air source at the second end of the fluid channel.

11. An apparatus according to claim 10, wherein the movable tip mould is movable in a linear direction from a first position where the tip mould is abutting the outer mould with the tip mould cavity aligned with the mould cavity to a second position at a predetermined distance from said first position via a sledge.

12. An apparatus according to claim 10, wherein a gap between the cooling blocks and the outer mould is provided at the second position in which cutting means are provided for cutting the moulded article away from the mould.

13. An apparatus according to claim 10, wherein the fluid channel is in controlled flow connection with the pressurized air source providing pressurized air through the fluid channel into the inner volume of the moulded article during the moulding process.

14. An apparatus according to claim 10, wherein the elongated central mould core is temperature controlled for maintaining an elevated temperature similar to that of the heated central mould.

15. An apparatus according to claim 14, wherein the movable tip mould part is temperature controlled for maintaining a temperature lower than of that the heated central mould.

16. An apparatus for injection moulding of an elongated hollow article, said apparatus comprising:
a heated central mould with an inlet opening for entering liquid moulding compound into a substantially tubular cavity formed in said central mould;

an elongated central mould core which is provided in the tubular cavity that extends beyond said tubular cavity and into a tip mould cavity of a tip mould part which is aligned with the tubular mould cavity in the longitudinal axis of the central mould core; wherein the tip mould part is moveable in a linear movement in a direction along the longitudinal axis of the elongated central mould core from a first position where the tip mould is abutting the outer mould with the tip mould cavity aligned with the mould cavity to a second position at a predetermined distance from said first position via a sledge wherein a set of cooling mould blocks are provided for encompassing and clamping the moulded portion of the article by radially inward movement when the tip mould is approaching said second position, wherein the cooling mould blocks are provided with inner contacting surfaces resembling the shape of the tubular mould cavity.

17. An apparatus according to claim 16, wherein the cooling moulding blocks are formed with end contacting surfaces having an end section geometry.

* * * * *